United States Patent [19]

Gandolfi et al.

[11] 4,220,759
[45] Sep. 2, 1980

[54] 13,14-DEHYDRO-11-DEOXY-PROSTAGLANDINS AND PROCESS FOR THEIR PREPARATION

[75] Inventors: Carmelo Gandolfi; Renato Pellegata; Franco Faustini; Angelo Fumagalli, all of Milan, Italy

[73] Assignee: Carlo Erba S.p.A., Milan, Italy

[21] Appl. No.: 57,518

[22] Filed: Jul. 13, 1979

Related U.S. Application Data

[62] Division of Ser. No. 664,472, Mar. 8, 1976, Pat. No. 4,198,430.

[30] Foreign Application Priority Data

Mar. 14, 1975 [IT] Italy ................................ 21264 A/75

[51] Int. Cl.$^3$ ............................................. C07D 307/77
[52] U.S. Cl. ................................... 542/426; 542/429; 542/430; 260/343.3 P; 260/346.22
[58] Field of Search ....................... 542/429, 426, 430; 260/343.3 P, 346.22

[56] References Cited

U.S. PATENT DOCUMENTS 4,041,064    8/1977    Gandolfi et al. ..................... 560/121

*Primary Examiner*—Robert Gerstl
*Attorney, Agent, or Firm*—Cushman, Darby & Cushman

[57] ABSTRACT

14-Halo lactone and lactol prostaglandin intermediates have been prepared.

1 Claim, No Drawings

13,14-DEHYDRO-11-DEOXY-PROSTAGLANDINS AND PROCESS FOR THEIR PREPARATION

This is a division of application Ser. No. 664,472, filed Mar. 8, 1976, now Pat. No. 4,198,430.

The present invention relates to optically active 13,14-dehydro-11-deoxy-prostaglandins, to a process for their preparation and to pharmaceutical compositions containing them.

The compounds of the invention have the general formula (I)

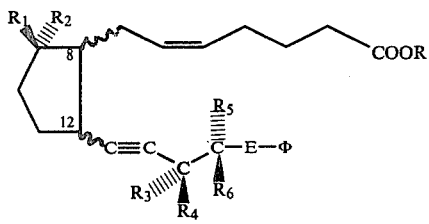 (I)

wherein
R is a member selected from the group consisting of hydrogen, a $C_1$—$C_{12}$ alkyl group, and a cation of a pharmaceutically acceptable base;
one of $R_1$ and $R_2$ is hydrogen and the other is hydroxy or acyloxy or $R_1$ and $R_2$ together form an oxo group;
one of $R_3$ and $R_4$ is hydrogen and the other is hydroxy;
$R_5$ and $R_6$ are independently selected from the group consisting of hydrogen, fluorine and $C_1$–$C_4$ alkyl, provided that when one of them is $C_1$–$C_4$ alkyl, the other is hydrogen or fluorine. and when one of them is fluorine, the other is $C_1$–$C_4$alkyl;
E is selected from the group consisting of —(CH$_2$)$_n$—, wherein n is an integer of 1 to 6, and —(CH$_2$)$_{n1}$—O—(CH$_2$)$_{n2}$—, wherein n$_1$ and n$_2$ are independently selected from the group consisting of zero, 1, 2 and 3.
Φ is a member selected from the group consisting of methyl; cycloalkyl containing 3 to 7 ring carbon atoms and optionally containing one or more ring oxygen or sulphur atoms; and phenyl unsubstituted or optionally substituted by one or more substituents selected from the group consisting of halogen, $C_1$–$C_4$alkoxy, phenyl, and trihalomethyl; and wherein the chains bound to the carbon atoms in the 8- and 12- positions have a trans-configuration.

The double bond in the 5(6)-position is a cis double bond. In the formulae of this specification, the broken lines ( ⫶⫶⫶⫶⫶ ) indicate that the substituents are in the α-configuration, i.e. are below the plane of the ring or of the chain, while the heavy solid lines ( ◂▬ ) indicate that the substituents are in the β-configuration, i.e. above the plane of the ring or of the chain; the wavy line attachment ( ⁀ ) indicates that the groups may be either in the α-configuration, i.e. below the plane of the ring, or in the β-configuration, i.e. above the plane of the ring. As stated above, the chains bound to the carbon atoms in the 8- and 12- positions must have a trans-configuration, i.e. these chains cannot be both in the α-configuration or both in the β-configuration; when one of them is in the α-configuration, the other is in the β-configuration and vice versa. As is evident from formula (I) the hydroxy group linked to the carbon atom in the 15-position may be either in the α-configuration

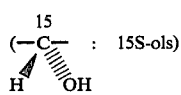

or in the β-configuration

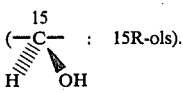

As stated above, only one alkyl group may be linked to the carbon atom in the 16-position, which alkyl group may be either a 16S-alkyl (α-configuration) or a 16R-alkyl (β-configuration).

Analogously, when on the carbon atom in the 16-position there is a fluorine atom, said substituent may be either a 16S-fluorine (α-configuration) or a 16R -fluorine (β-configuration).

New compounds of the invention are therefore optically active compounds having the general formulae (Ia) and (Ib)

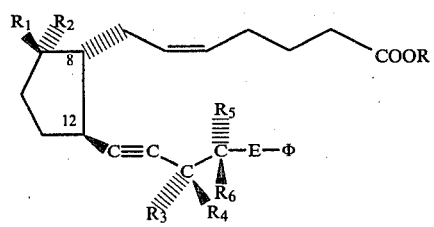   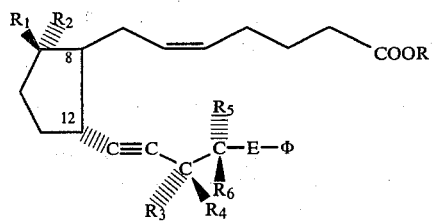

(Ia: nat-compounds)   [Ib: ent (or 8,12-diiso)-compounds]

The alkyl and alkoxy groups may be branched or straight chain groups.

When R is a $C_1$—$C_{12}$ alkyl group, it is preferably methyl, ethyl, propyl or heptyl. Preferably, one of $R_1$ and $R_2$ is hydrogen and the other is hydroxy or $R_1$ and $R_2$, taken together, form an oxo group.

When one of $R_1$ and $R_2$ is acyloxy, it is preferably an alkanoyloxy group containing up to 6 carbon atoms, a benzoyloxy or a p-phenyl-benzoyloxy group.

When one of $R_5$ and $R_6$ is a $C_1$—$C_4$ alkyl group, it is preferably methyl. When E is —(CH$_2$)$_n$— and Φ is methyl, n is preferably 4, 5 or 6; when E is —(CH$_2$)$_n$— and Φ is cycloalkyl or phenyl, n is preferably 2.

When E is —(CH$_2$)$_{n1}$—O—(CH$_2$)$_{n2}$, it is preferably, when Φ is alkyl, —CH$_2$—O—CH$_2$—CH$_2$—, while, when Φ is cycloalkyl or phenyl, E is preferably —CH$_2$—O—.

Preferably Φ is methyl, cyclopentyl, cyclohexyl and phenyl.

When Φ is a trihalomethyl-substituted phenyl, the trihalomethyl group is preferably trifluoromethyl or trichloromethyl.

Examples of cations of pharmaceutically acceptable bases are either metallic cations, such as sodium, potassium, calcium and aluminium or organic amine cations, such as trialkylamines.

The compounds of formula (I) are prepared by deetherifying a compound of general formula (II)

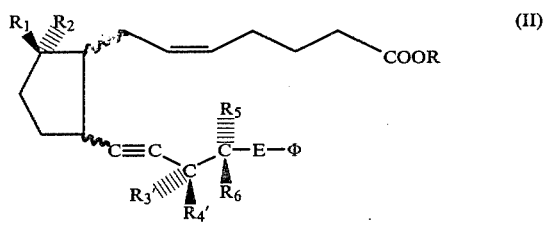

(II)

wherein R, $R_1$, $R_2$, $R_5$, $R_6$, E and Φ are as defined above, and one of $R'_3$ and $R'_4$ is a known protecting group bound to the chain by an ethereal oxygen atom, and the other is hydrogen, and wherein the chains bound to the carbon atoms in the 8- and 12- positions have a trans-configuration; and if desired converting a compound of formula (I) into another compound of formula (I) by known methods.

The deetherification reaction is peformed under conditions of mild acid hydrolysis, for example with mono- or poly- carboxylic acids, e.g. formic, acetic, oxalic, citric and tartaric acid, and in a solvent, for example water, acetone, tetrahydrofuran, dimethoxyethane and lower aliphatic alcohols.

Preferably, a 0.1 N to 0.25 N poly-carboxylic acid (e.g. oxalic or citric acid) solution is used in the presence of a convenient low boiling co-solvent which is miscible with water and which can be easily removed in vacuo at the end of the reaction.

The known protecting groups (i.e. ether groups) should be convertible to hydroxy groups under mild reaction conditions, e.g. acid hydrolysis. Examples are acetalic ethers, enolethers and sylylethers. The preferred groups are:

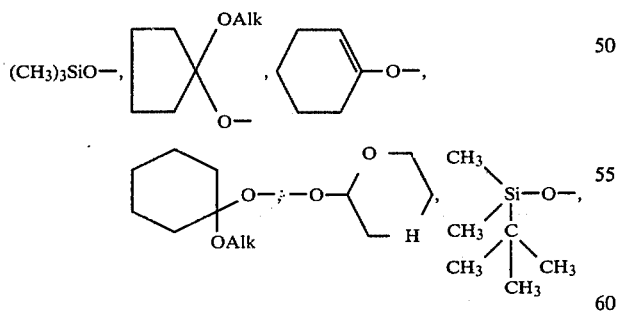

wherein W is —O— or —CH$_2$—, and Alk is a lower alkyl group.

As stated above, a compound of formula (I) may be converted into another compound of formula (I) by known methods, for example a compound of formula (I) wherein R is a $C_1$–$C_{12}$ alkyl group, may be hydrolysed, in an acid or basic medium, to give a compound of formula (I) wherein R is hydrogen. Thus a compound of formula (I) wherein R is hydrogen may be reacted with a base to give a compound of general formula (I) wherein R is a cation, or a compound of general formula (I) wherein R is hydrogen may be esterified to give a compound of general formula (I) wherein R is a $C_1$–$C_{12}$ alkyl group.

The compound of formula (II) may be prepared by a multi-step process, starting from a lactone of formula (III)

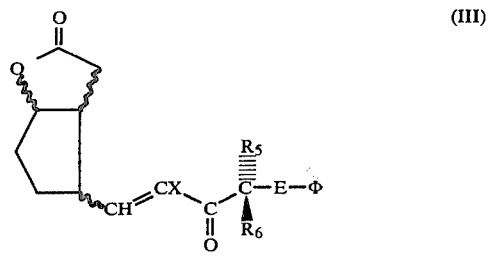

(III)

wherein $R_5$, $R_6$, E and Φ are as defined above, and X is chlorine, bromine, iodine; and wherein the lactone ring is in the trans-configuration with respect to the side chain, and wherein the hydrogen atom linked to the carbon atom in the 13-position (prostaglandin numbering) and the halogen atom linked to the carbon atom in the 14-position (prostaglandin numbering) are preferably in the trans-position (geometric trans-isomers).

The halo-lactone of formmula (III) may be therefore either a compound of formula (IIIa)

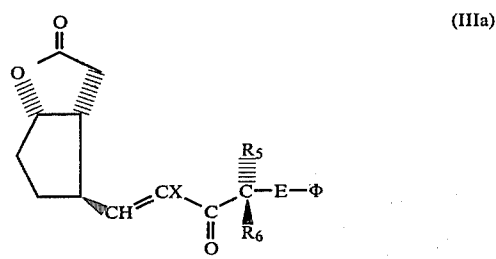

(IIIa)

or a compound of formula (IIIb)

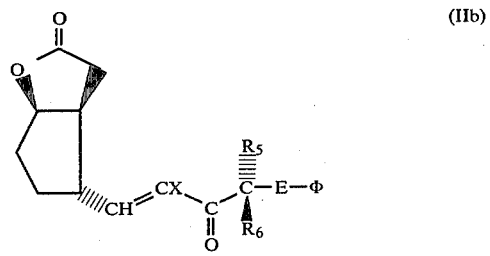

(IIb)

The multi-step process to obtain the compound of formula (II) involves the following steps:

(a) reduction of the 15-oxo-group (prostaglandin numbering) of the halo-lactone of formula (III) to yield a mixture of the 15S- and 15R- ols having the formulae (IVa) and (IVb)

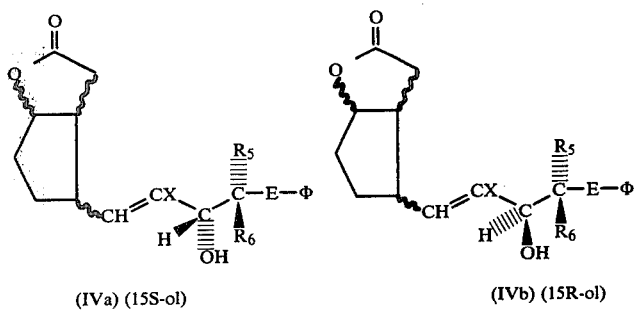

(IVa) (15S-ol)    (IVb) (15R-ol)

wherein X, $R_5$, $R_6$, E and $\Phi$ are as defined above.

The reduction of the 15-oxo-group may be suitably performed in an organic solvent, such as methanol, diethyl ether, dimethoxyethane, dioxan, tetrahydrofuran, benzene, and their mixtures, by using e.g. metal borohydrides, in particular sodium borohydride, lithium borohydride, zinc borohydride, triisobutyl-lithium borohydride and triisobutyl-potassium borohydride.

(b) Separation of the 15S-ol from the 15R-ol. This separation may be performed by column chromatography, e.g. silica gel chromatography, or by thin-layer chromatography, using, in both cases, as eluents, mixtures of methylene chloride/ethylether or of cyclohexane/ethylether, as well as by fractionated crystallization, for example from ethylether or isopropyl ether, so as to obtain pure optically active antipodes having the following formulae:

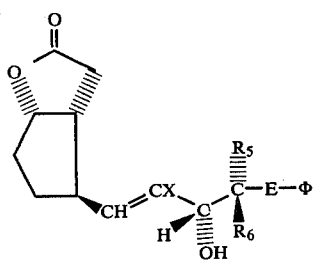

(IV'a)

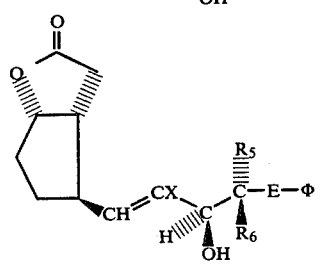

(IV'b)

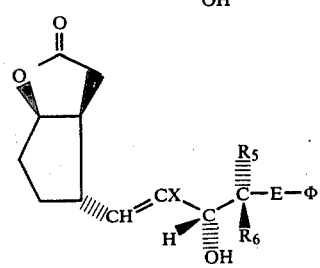

(IV''a)

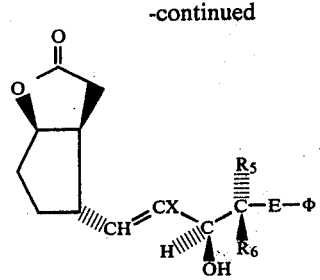

-continued (IV''b)

(c) Conversion of an optically active compound of formula (V)

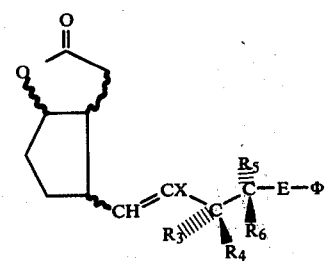

(V)

wherein

X, $R_5$, $R_6$, E and ; $\Phi$ are defined above, and one of $R_3$ and $R_4$ is hydrogen and the other is hydroxy, into an optically active compound of formula (VI)

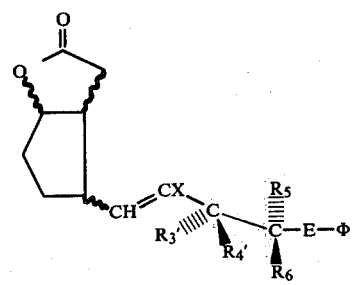

(VI)

wherein

X, $R_5$, $R_6$, E and $\Phi$ are as defined above, and one of $R'_3$ and $R'_4$ is hydrogen and the other is a known protecting group bound to the chain through an ethereal oxygen atom.

The etherification of the compound of formula (V) is preferably carried out with a vinylic ether of formula

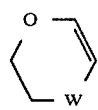

(VII)

wherein W is —O— or —CH₂—, in the presence of catalytic amounts of for example p-toluenesulphonic acid or benzenesulphonic acid, or with a silyl ether, for instance by reacting a trisubstituted chlorosilane in the presence of a base (for example imidazole or a trialkylamine) as acceptor of the hydrohalic acid formed, or with an enol ether, for instance by reaction, in the presence of an acid catalyst, with a cyclopentanone or cyclohexanone diacetal, at the reflux temperature in an inert solvent and distilling off the alcohol formed to obtain mixed acetals or enol ethers, according to the amount of catalyst used or the heating time.

Other vinylic ethers which may be used are 3-methoxy-5,6-dihydro-2H-pyran and 4-methoxy-5,6-dihydro-2H-pyran.

(d) Reduction of the compound of formula (VI) to give an optically active lactol of formula (VIII)

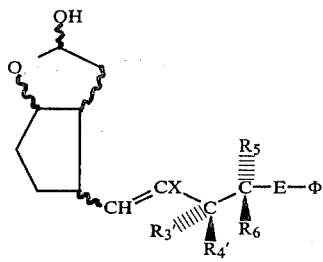

(VIII)

wherein X, $R'_3$, $R'_4$, $R_5$, $R_6$, E and $\Phi$ are as defined above.

The reduction may be performed by treatment with diisobutylaluminium hydride or sodium bis-(2-methoxyethoxy)-aluminium hydride in an inert solvent, such as toluene, n-heptane, n-hexane, benzene or their mixtures, at below $-30°$ C.

(e) Reaction of the lactol of formula (VIII) with a Wittig reagent comprising a group of formula —(CH₂)₄—COOR wherein R is a hydrogen atom or a $C_1$—$C_{12}$ alkyl group, to give an optically active compound of formula (IX)

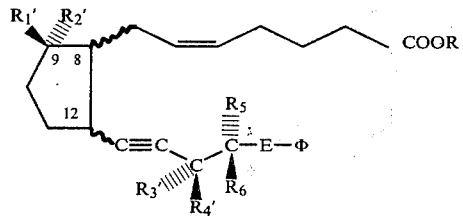

(IX)

wherein R, $R'_3$, $R'_4$, $R_5$, $R_6$, E and $\Phi$ are as defined above, wherein in the nat-derivatives, $R'_1$ is hydrogen and $R'_2$ is hydroxy, while in the ent-derivatives, $R'_1$ is hydroxy and $R'_2$ is hydrogen, and wherein the chains bound to the carbon atoms in the 8- and 12- positions have the trans-configuration. When the lactol used for the Wittig reaction has the herebelow-reported formula (VIII)

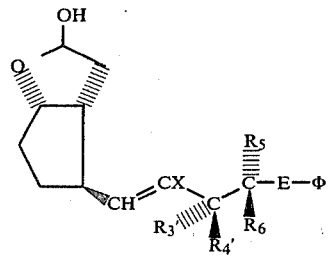

(VIIIa)

nat-derivative of formula (IX) is obtained, wherein $R'_1$ is hydrogen and $R'_2$ is hydroxy, while when the lactol used as starting material has the herebelow-reported formula (VIIIb)

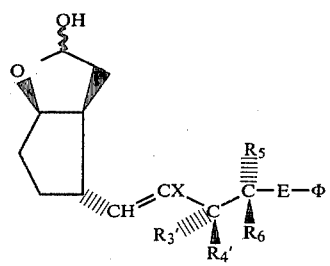

(VIIIb)

an ent-derivative of formula (IX) is obtained, wherein $R'_1$ is hydroxy and $R'_2$ is hydrogen.

In the lactol of formula (VIII), the hydrogen atom linked to the carbon atom in the 13-position (prostaglandin numbering) and the hydrogen atom linked to the carbon atom in the 14-position (prostaglandin numbering) may be either in the trans-position (geometric trans-isomers) or in the cis-position (geometric cis-isomers). Preferably they are in the trans-position, since in the above-reported method for the preparation of the lactol of formula (VIII) the geometric trans-isomers are obtained in a far higher percentage (92–95%), while the geometric cis-isomers are obtained in a far lower percentage (5–8%).

The Wittig reaction is performed by using the conditions generally followed for this kind of reaction, i.e. in an organic solvent, for example diethylether, hexane, dimethylsulphoxide, tetrahydrofuran, dimethylformamide, or hexamethylphosphoramide, in the presence of a base, preferably sodium hydride or potassium tert-.butoxide, at 0° C. to the reflux temperature of the reaction mixture, preferably at room temperature or below.

When in the lactol of formula (VIII) X is bromine or iodine, the Wittig reaction may be performed using about two moles of Witting reagent per mole of lactol and it is sufficient that the reaction lasts 10–20 minutes. When in the lactol of formula (VIII) X is chlorine, it is necessary, by using for example 1.5 to 2.5 moles of Wittig reagent per mole of lactol, to prolong the reaction time up to ten hours or, if it is desired to use shorter reaction times, it is necessary to employ a great excess of Wittig reagent (at least 5 moles of Wittig reagent per mole of lactol for reaction times of about 30 minutes).

Preferably, in the lactol of formula (VIII) X is bromine or iodine, since in this case both the triple bond formation and the alkylation with the Wittig reagent take place at the same time, in an only one step, by employing little amounts of the Wittig reagent and short reaction times. The term "Wittig reagent" includes compounds of general formula

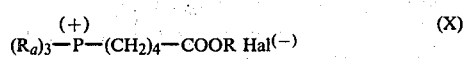

wherein $R_a$ is aryl or alkyl, Hal is bromine or chlorine and R is hydrogen or $C_1$–$C_{12}$ alkyl. When $R_a$ is alkyl, it is preferably ethyl.

The preparation of the Wittig reagents is discussed in detail by Tripett, Quart. Rev., 1963, XVII, No. 4,406.

(f) Optional esterification of the compound of formula (IX), wherein R is $C_1$–$C_{12}$ alkyl, to give the 9α- or 9β-acyloxy derivative.

The esterification may be performed by conventional methods, for example by reaction with an acid halide or anhydride, in the presence of a base. In this case, starting from a nat-derivative of formula (IX) wherein $R'_1$ is hydrogen and $R'_2$ is hydroxy, a 9α-acyloxy nat-derivative is obtained, while starting from an ent-derivative of formula (IX), wherein $R'_1$ is hydroxy and $R'_2$ is hydrogen, a 9β-acyloxy ent-derivative is obtained.

On the contrary, when the esterification is carried out with a carboxylic acid in the presence of a compound of formula $M^{\nu}Y_3$, wherein $M^{\nu}$ is a metalloid of the V group and Y is an alkyl, a dialkylamino or an aryl group, and of a hydrogen acceptor agent, starting from a nat-derivative of formula (IX) wherein $R'_1$ is hydrogen $R'_2$ is hydroxy, a 9β-acyloxy nat-derivative is obtained, while starting from an ent-derivative of formula (IX) wherein $R'_1$ is hydroxy and $R'_2$ is hydrogen, a 9α-acyloxy ent-derivative is obtained. That is, in the latter case, the esterification reaction involves the complete inversion of configuration of the hydroxy group in the 9-position; the reaction is preferably carried out at room temperature in an inert anhydrous solvent, preferably selected from the group consisting of aromatic hydrocarbons, such as benzene and toluene, linear or cyclic ethers, for example diethyl ether, dimethoxyethane, tetrahydrofuran and dioxan, and halogenated hydrocarbons, such as dichloromethane and dichloroethane. All the used reagents, that are the compounds of formula $M^{\nu}Y_3$, the esterifying carboxylic acid and the hydrogen-acceptor agent, are employed in the proportion of at least 1.5 mole per each mole of alcohol; 2 to 4 moles of the reagents per each mole of alcohol are preferably used.

In the compound of formula $M^{\nu}Y_3$, $M^{\nu}$ is preferably P, As, Sb, especially P. Again in the same compound, when Y is alkyl, it is preferably methyl, while when Y is aryl, it is perferably phenyl; when Y is dialylamino, it is preferably dimethylamino. The compound of formula $M^{\nu}Y_3$ is preferably selected from the group consisting of triphenylphosphine, triphenylarsine, triphenylstibine and hexamethyltriaminophosphine of formula $[(CH_3)_2N]_3P$.

The hydrogen-acceptor used is preferably an ester or an amide of the azodicarboxylic acid, preferably ethyl azodicarboxylate, but also other hydrogen-acceptors may be used, for instance 2,3,5,6-tetrachloro-benzoquinone, 2,3-dicyano-5,6-dichloro-benzoquinone or azobisformamide.

(g) Saponification of the 9α- or 9β-acyloxy groups to yield free 9α- or 9β-hydroxy groups and optional saponification also of the carbalkoxy group at the end of the α-chain to yield compounds wherein R is hydrogen.

The saponification is carried out by the usual methods, for example by using inorganic bases.

(h) Optional conversion of the compounds obtained according to the preceding step (g) wherein R is hydrogen into compounds wherein R is a cation of a pharmaceutically acceptable base. Also this conversion is carried out by conventional methods, for example by salification with a base at room temperature in water or in a solvent miscible with water and then removal of the solvent by evaporation.

(i) By the steps (e), (f), (g) and (h) there is obtained an optically active compound of formula (II) wherein one of $R_1$ and $R_2$ is hydrogen and the other is hydroxy or acyloxy, R is a member selected from the group consisting of hydrogen, a $C_1$–$C_{12}$ alkyl group, and the cation of a pharmaceutically acceptable base, $R'_3$, $R'_4$, $R_5$, $R_6$, E and Φ are as defined above; the so obtained compound of formula (II) wherein one of $R_1$ and $R_2$ is hydrogen and the other is hydroxy and R, $R'_3$, $R'_4$, $R_5$, $R_6$, E and Φ are as defined above, is then oxidized in the 9-position to give an optionally active compound of formula (II), wherein $R_1$ and $R_2$ together form an oxo group, and R, $R'_3$, $R'_4$, $R_5$, $R_6$, E and Φare as defined above.

The oxidation may be carried out with, for example, Jones reagent or Moffatt reagent.

The halo-lactone of formula (III) may be in turn prepared in an only one step by reaction of an optically active or racemic aldehyde of formula (XI)

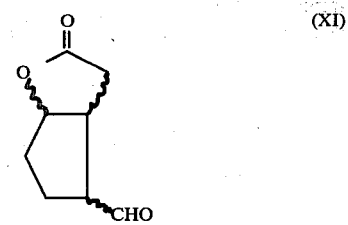

with an optically active phosphonate of formula (XII)

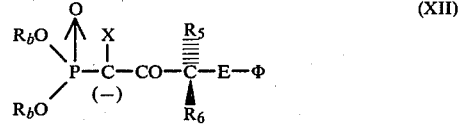

wherein $R_b$ is an alkyl group, X, $R_5$, $R_6$, E and Φ are as defined above.

The reaction is suitably performed in a dry solvent which is preferably benzene, dimethoxyethane, tetrahydrofuran, dimethylformamide or their mixtures, in an inert gas atmosphere, and using a suspension of 1.5–2.5 molar equivalents of the compound of formula (XII) per each mole aldehyde. Starting material for this one-step process may therefore be an aldehyde of formula (XIa)

or an aldehyde of formula (XIb)

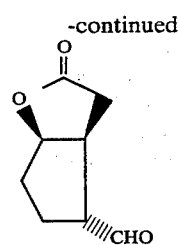

The aldehydes of formulae (XIa) and (XIb) may be prepared starting from the compounds of formulae (XIIIa) and respectively (XIIIb)

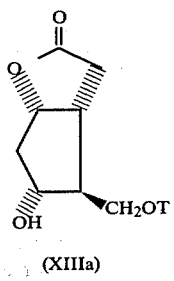 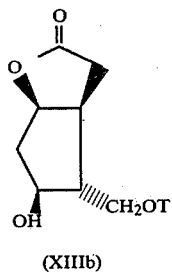

wherein T is a member selected from the group consisting of lower alkyl, benzyl, tetrahydropyranyl, dioxanyl, dimethyl-tert.-butyl-silyl, by reaction with a mixture of iodosuccinimide and triphenylphosphine or a mixture of triphenylphosphite and methyliodide, so obtaining compounds of formulae (XIVa) and respectively (XIVb)

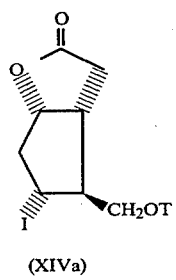 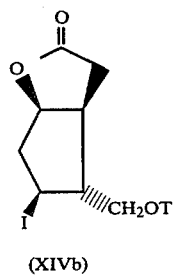

wherein T is as defined above, which are then reduced, by using e.g. sodium cyanoborohydride or sodium borohydride in dimethylsulphoxide, to give compounds of formulae (XVa) and respectively (XVb)

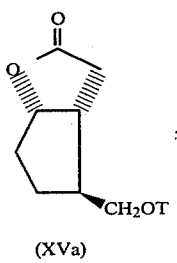 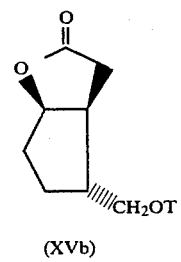

wherein T is as defined above, which are then converted into the corresponding compounds having the free hydroxy group, which are finally oxidized to give the aldehydes of formulae (XIa) and respectively (XIb).

The conversion of compounds of formulae (XVa) and (XVb) into compounds having the free hydroxy group may be performed by treatment with e.g. BBr₃ in a suitable solvent such as methylene chloride or ethylacetate when T is lower alkyl or benzyl, while when T has the other above-reported meanings, the conversion may be performed for example by mild acid hydrolysis.

The oxidation to give the aldehydes of formulae (XIa) and (XIb) may be performed for example with Moffatt reagent or with Collins reagent. The compound of formula (XIIIa) (optically active or racemic derivative) may be prepared substantially as described by E. J. Corey, New York Acad. Sciences 180, 24 (1971), while the compound of formula (XIIIb) may be prepared as described in British Pat. Spec. No. 1,420,338.

Alternatively, the compounds of formulae (XIIIa) and (XIIIb) may be prepared starting from iodo-hydroxy-lactones of formulae (XVIa) and (XVIb), respectively

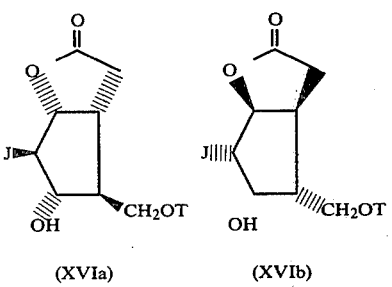

wherein T is as defined above, by reaction with a compound of formula $M^v Y_3$ wherein $M^v$ and Y are as defined above, and a carboxylic acid in an inert anhydrous solvent, such as benzene, toluene, dioxan, dichloromethane in the presence of a hydrogen-acceptor agent, for example an ester or an amide of the azodicarboxylic acid, so obtaining compounds of formulae (XVIIa) and (XVIIb) respectively

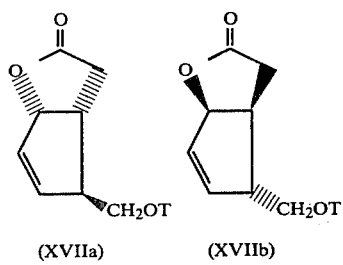

wherein T is as defined above, which after saponification with a base, such as NaOH, in aqueous methanol, are hydrogenated e.g. with Pt O₂, to give, after acidification, e.g. with hydrochloric acid, the compounds of formulae (XIIIa) and (XIIIb), respectively.

The racemic or optically active iodo-hydroxy-lactone of formula (XIVa) may be prepared by treating a compound of formula (XVIIIa)

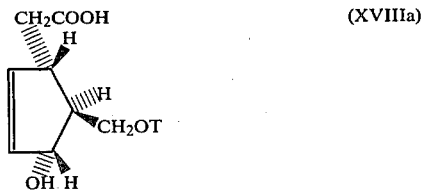

wherein T is as defined above, in the form of a salt, e.g. with an alkali metal, with an aqueous solution of potassium triiodide at room temperature.

The optically active compound of formula (XVIIIa) i.e. the dextrorotatory antipode may be prepared by resolution with optically active bases, e.g. dehydroabiethylamine of the compound of formula (XIX)

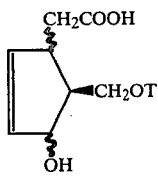

(XIX)

wherein T is as defined above, mixture of both optical antipodes (laevorotatory and dextrorotatory), whose preparation is described by Corey et al, J. Am. Chem. Soc. 1969, 91, 5675; ibid. 1971, 93, 1489; ibid. 1971, 93, 4326.

Also the iodo-hydroxy-lactone of formula (XIVb) may be prepared following the same method, starting on the contrary from the laevorotatory antipode of formula (XVIIIb)

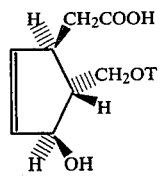

(XVIIIb)

wherein T is as defined above, as described in British Pat. Spec. No. 1,420,338.

Alternatively, the aldehydes of formulae (XIa) and (XIb) may be prepared by reacting compounds of formulae (XIIIa) and (XIIIb), respectively, with a sulphonic acid halide, to give compounds of formulae (XXa) and respectively (XXb)

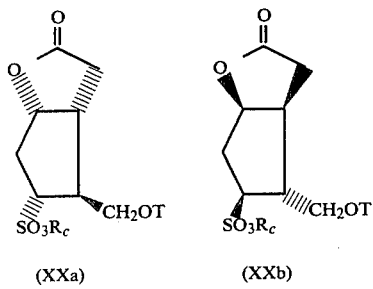

(XXa)    (XXb)

wherein T is as defined above, and Rc is the residue of the sulphonic acid, for example methyl, phenyl and p-tolyl, which by treatment with $MgI_2$ in diethyl ether yield compounds of formulae (XIVa) and respectively (XIVb) which, as reported above, are reduced, then converted into the corresponding compounds having the free hydroxy group and finally oxidized to give the aldehydes of formulae (XIa) and (XIb), respectively.

Alternatively, the compounds of formulae (XVIIa) and (XVIIb) may be obtained by reacting the compounds of formulae (XXa) and, respectively, (XXb), in an organic solvent, such as acetone, with a dibasic oxalate of a quaternary ammonium salt.

The phosphonate carbanion of formula (XII) may be in turn prepared by reacting an optically active phosphonate of formula (XXI)

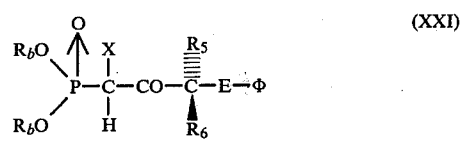

(XXI)

wherein $R_b$, X, $R_5$, $R_6$, E and $\Phi$ are as defined above, with an equivalent of a base preferably selected from the group consisting of sodium hydride, lithium hydride, calcium hydride, an alkyl-lithium derivative and the anion $CH_3-SO_2-CH_2^{(-)}$.

The phosphonate of formula (XXI) may be obtained by halogenation of a phosphonate of formula (XXII)

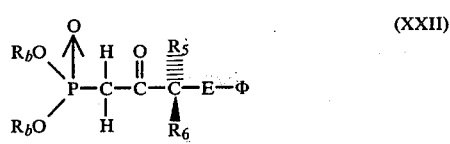

(XXII)

wherein $R_b$, $R_5$, $R_6$, E and $\Phi$ are as defined above.

The halogenation may be carried out in a conventional manner, operating substantially as in the halogenation of β-ketoesters.

The phosphonate of formula (XXII) may be prepared by known methods, e.g. according to E. J. Corey et al, J. Am. Chem. Soc. 90, 3247 (1968) and E. J. Corey and G. K. Kwiatkowsky, J. Am. Chem. Soc., 88, 5654 (1966). Preferably, the phosphonate of formula (XXII) is prepared by reaction of a compound of formula (XXIII)

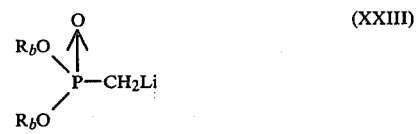

(XXIII)

wherein $R_b$ is defined above, with a compound of formula (XXIV)

(XXIV)

wherein $R_d$ is alkyl, and $R_5$, $R_6$, E and $\Phi$ are as defined above. When in the compound of formula (XXIV), the carbon atom bearing the $R_5$ and $R_6$ substituents is an asymmetric carbon atom, there is used for the reaction with the compound of formula (XXIII) either one or the other of the optical antipodes and not the racemic compound.

Alternatively, the halo-phosphonate carbanion of formula (XII) may be prepared by reacting the phosphonate carbanion of formula (XXV)

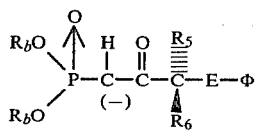

(XXV)

wherein $R_b$, $R_5$, $R_6$, E and Φ are as defined above, with a halogenating agent selected from the group consisting of $Br_2$, pyrrolidone-hydrotribromide (PHTB), dioxandibromide, N-chloroacetamide, N-chlorosuccinimide, N-bromosuccinimide, N-bromoacetamide, N-bromocaprolactame, and N-iodosuccinimide.

By using the imides as halogenating agents, the carbanion of the halo-phosphonate of formula (XII) is obtained directly with the use of only one equivalent of base; otherwise, it should be necessary to use another equivalent of a base to obtain the carbanion of the halophosphonate.

The phosphonate carbanion of formula (XXV) may be in turn obtained by treatment of the phosphonate of formula (XXII) with an equivalent of a base, e.g. sodium, lithium or calcium hydride.

Among the intermediates described in this specification, the following are compounds of the invention:

(1) the compound of general formula (XXVI)

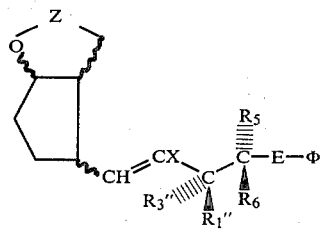

(XXVI)

wherein Z is >C=O or

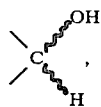

one of $R''_3$ and $R''_4$ is hydrogen and the other is a hydroxy group or a known protecting group bound to the chain by an etheral oxygen atom or, when Z is >C=0, $R''_3$ and $R''_4$, taken together, may also be an oxo group, and wherein X, $R_5$, $R_6$, E and Φ are as defined above;

(2) a compound of formula (II), wherein R, $R_1$, $R_2$, $R'_3$, $R'_4$, $R_5$, $R_6$, E and Φare as defined above.

The compound (XXVI) wherein Z is

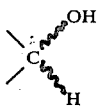

and one of $R''_3$ and $R''_4$ is hyrogen and the other is hydroxy, may be prepared by deetherifying, in the above-reported reaction conditions, a compound of formula (VIII). The compounds of formula (I) may be used for the same therapeutical indications as natural prostaglandins, with respect to which, however, they offer the advantage of being no substrates for the enzyme 15-prostaglandin dehydrogenase, which, as is known, quickly inactivates natural prostaglandins, and, furthermore, are characterized by a more selective therapeutical action.

The compounds of formula (I), furthermore, competitively inhibit the use of natural prostaglandins as substrate by the same enzyme.

In particular, the compounds of the invention are able to inhibit in humans gastric secretion as well as to prevent formation of ulcerogenic lesions in the gastrodudodenal tract at sufficiently low dosages with a very favourable therapeutic index (6 to 20 times) as far as the ratio between the therapeutical dose and the lowest dose inducing side effects (i.e. emesis and diarrhea) is concerned.

The compounds of the invention, for example, 11-deoxy-16S-methyl-13,14-dehydro-PGE$_2$ (i.e. 5c-9-oxo-15S-hydroxy-16S-methyl-prost-5-en-13-ynoic acid), and its 15-epi derivative (i.e. 5c-9-oxo-15R,-hydroxy-16S-methyl-prost-5-en-13-ynoic acid), 11-deoxy-16S-methyl-13,14-dehydro-15-epi-ent-PGE$_2$ (i.e. 5-c-9-oxo-15S-hydroxy-16S-methyl-8,12-diiso-prost-5-en-13-ynoic acid) and 11-deoxy-16R-methyl-13,14-dehydro-15-epi-ent-PGE$_2$ (i.e. 5c-9-oxo-15S-hydroxy-16R-methyl-8,12-diiso-prost-5-en-13-ynoic acid), differently from PGE$_2$ taken as the standard compound, are fully unable to stimulate smooth muscles, such as the ileum of guinea-pigs, the colon of gerbils and the uterus of rats, while, when administered, for instance subcutaneously, they are able to prevent stress-induced ulcerogenic lesions and to reduce gastric secretion (pyloric ligature test according to Shay) (H. Shay et al., Gastroenter., 26, 906 (1954)), as shown by the following Table:

TABLE

| Compound | In vitro test: gerbil colon, guinea-pig ileum, rat uterus | Stress-induced ulcera | Antisecretory activity |
|---|---|---|---|
| PGE$_2$ | 1 | 1 | 1 |
| 11-deoxy-16S-methyl-13,14-dehydro-PGE$_2$ | <0.01 | 7.25 | 4.2 |
| 11-deoxy-16S-methyl-13,14-dehydro-15-epi-PGE$_2$ | <<0.01 | 0.5 | 0.46 |
| 11-deoxy-16R-methyl-13,14-dehydro-15-epi-ent-PGE$_2$ | <0.01 | 2.3 | 2.8 |
| 11-deoxy-16S-methyl-13,14-dehydro-15-epi-ent-PGE$_2$ | <0.01 | 1.8 | 2.7 |

The same compounds are also indicated as oestrum-inducing and ovulation-regulating agents as well as in the treatment of hypertension and circulatory and respiratory disorders.

The compounds of formula (I) can be administered orally, parenterally, or by intravenous or intrauterine (extra-amniotic or intra-amniotic) way, by rectal suppositories or by inhalation. For example, they can be administered by intravenous infusion of a sterile isotonic saline solution at the rate of 0.01 to 10, preferably 0.05 to 1, μg/kg of mammal body weight per minute.

The invention therefore also provides a pharmaceutical composition comprising a compound of formula (I) and a pharmaceutically acceptable carrier or diluent.

The compositions may be prepared by conventional methods and can be, for example, in the form of tablets, capsules, pills, suppositories or bougies, or in liquid form e.g. solutions, suspensions or emulsions.

Examples of substances which can serve as carriers or diluents are water, gelatin, lactose, starches, magnesium stearate, talc, vegetable oil, benzyl alcohol and cholesterol.

The invention is illustrated by the following examples, where the abbreviations THP, DIOX, DMSO, THF, DMF, DIBA, HMPA, Et$_2$O, DME, respectively, refer to tetrahydropyranyl, dioxanyl, dimethylsulphoxide, tetrahydrofuran, dimethylformamide, diisobutylaluminium hydride, hexamethylenephosphoramide, ethyl ether and dimethoxyethane.

EXAMPLE 1

Under nitrogen, with all humidity excluded, a suspension of 0.15 g of NaH (80% dispersion in mineral oil) in 13 ml of DMSO is heated at 58°–65° until no more hydrogen evolves. After cooling to 4°–8°, 3.3 g of triphenyl-(4-carboxybutyl)-phosphonium bromide is added and the mixture stirred until it is all dissolved, with formation of a dark red solution of the carbanion of $(C_6H_5)_3P\text{—}^{(-)}CH\text{—}(CH_2)_3\text{—}COO^{(-)}$, which is maintained by external cooling at temperature of about 10°–12° C.

To this is added a solution of 0.58 g of 2α-hydroxy-5β-(2'-bromo-3'S-hydroxy-1'R-methyl-oct-1'-trans-1'-enyl)-cyclopenten-1α-ethanal-γ-lcatol-3'-(1''-methoxy-4''-THP-ether) in 4 ml of anhydrous DMSO and the mixture stirred for 4 hours, then diluted with 20 ml of water and extracted 16 times with 3ml aliquote of ethyl ether to remove the triphenylphosphoxide formed. The combined ether extracts are re-extracted 4 times with 3 ml aliquote of 0.5 N NaOH and discarded. The combined aqueous alkaline extracts are acidified to pH 4.5 with 2 N sulfuric acid and extracted with 1:1 ethyl ether:pentane. The combined organic extracts are washed until neutral and dried over sodium sulfate, yielding 0.61 g of 5c9α,15S-dihydroxy-16R-methyl-prost-5-en-13-ynoic acid-15-(4'-methoxy-4'-THP-ether).

By the same procedure, starting from the 3'acetalic ethers (as 3'-DIOX-ethers, 3'-THP-ethers, 3'-(4''-methoxy-4''-THP-ethers, and 3'-(3''-methoxy-3''-THP-ethers) of the following 2α-hydroxy-cyclopentan-1α-ethanal-γ-lactols:

(2'-bromo-3'S-hydroxy-oct-1'-trans-1'-enyl);
(2'-bromo-3'S-hydroxy-non-1'-trans-1'-enyl);
(2'-bromo-3'S-hydroxy-4'S-methyl-oct-1'-trans-1'-enyl);
(2'-bromo-3'S-hydroxy-4'R-methyl-non-1'-trans-1'-enyl);
(2'-bromo-3'S-hydroxy-4'R-methyl-5'-cyclohexyl-pent-1'-trans-1-enyl);
(2'-bromo-3'S-hydroxy-dec-1'-trans-1'-enyl);
(2'-bromo-3'S-hydroxy-5'-oxa-oct-1'-trans-1'-enyl);
(2'-bromo-3'S-hydroxy-5'-oxa-non-1'-trans-1'-enyl);
(2'-bromo-3'S-hydroxy-4'R-methyl-5'-oxa-oct-1'-trans-1'-enyl);
(2'-bromo-3'S-hydroxy-4'S-methyl-5'-oxa-non-1'-trans-1'-enyl);
(2'-bromo-3'S-hydroxy-5'-cyclopentyl-pent-1'-trans-1'-enyl);
(2'-bromo-3'S-hydroxy-5'-cyclohexyl-pent-1'-trans-1'-enyl);
(2'-bromo-3'S-hydroxy-5'-p-chlorophenyl-pent-1'-trans-1'-enyl);
(2'-bromo-3'S-hydroxy-5'-phenyl-pent-1'-trans-1'-enyl);
(2'-bromo-3'S-hydroxy-4'-cyclohexyl-but-1'-trans-1'-enyl);
(2'-bromo-3'S-hydroxy-4'-phenoxy-but-1'-trans-1'-enyl);

were obtained as the 3'-(DIOX-ethers, 3'-THP-ethers, 3'-(4'''-methoxy-4''-THP-ethers and as the 3'-(3''-methoxy-3''-THP-ethers) of the following prostenynoic acids and the 15-acetalic ethers (DIOX-ethers, THP-ethers, 4'-methoxy-4'-THP-ethers, 3'-methoxy-3'-THP-ethers) were obtained of the 15-acetalic ethers (DIOX-ethers, THP-ethers, 4'-methoxy-4'-THP-ethers, 3'-methoxy-3'-THP-ethers) of the following compounds:

5c-9α,15S-dihydroxy-prost-5-en-13-ynoic acid;
5c-9α,15S-dihydroxy-20-methyl-prost-5-en-13-ynoic acid;
5c-9α,15S-dihydroxy-16S-methyl-prost-5-en-13-ynoic acid;
5c-9α,15S-dihydroxy-16R,20-dimethyl-prost-5-en-13-ynoic acid;
5c-9α,15S-dihydroxy-16R-methyl-1S,19,20-trinor-17-cyclohexyl-prost-5-en-13-ynoic acid;
5c-9α,15S-dihydroxy-20-ethyl-prost-5-en-13-ynoic acid;
5c-9α,15S-dihydroxy-17-oxa-prost-5-en-13-ynoic acid;
5c-9α,15S-dihydroxy-17-oxa-20-methyl-prost-5-en-13-ynoic acid;
5c-9α,15S-dihydroxy-17-oxa-16R-methyl-prost-5-en-13-ynoic acid;
5c-9α,15S-dihydroxy-18,19,20-trinor-17-cyclopentyl-prost-5-en-13-ynoic acid;
5c-9α,15S-dihydroxy-18,19,20-trinor-17-phenyl-prost-5-en-13-ynoic acid;
5c-9α,15S-dihydroxy-18,19,20-trinor-17-p-chlorophenyl-prost-5-en-13-ynoic acid;
5c-9α,15S-dihydroxy-18,19,20-trinor-17-phenyl-prost-5-en-13-ynoic acid;
5c-9α,15S-dihydroxy-17,18,19,20-tetranor-16-cyclohexyloxy-prost-5-en-13-ynoic acid;
5c-9α,15S-dihydroxy-17,18,19,20-tetranor-16-phenoxy-prost-5-en-13-ynoic acid.

EXAMPLE 2

A solution of the ylide obtained by the procedure described in example 1, starting with 0.612 g of NaH (80% dispersion in mineral oil) and 5.32 g of triphenyl-(4-carboxybutyl)-phosphonium bromide in 27 ml of DMSO is treated with a solution of 1.52 g of 2β-hydroxy-cyclopentyl-1β-ethanal acid-γ-lactol-5α-(2'-bromo-3'S-hydroxy-4'R-methyl-non-1'-trans-1'-enyl)-3'-DIOX-ether in 6 ml of anhydrous DMSO. After 10 hours at room temperature, it is diluted with 35 ml of water, acidified to pH 4.8 and extracted with ethyl ether:pentane 1:1. The aqueous phase is discarded and the organic extracts are re-extracted with 0.2 N KOH. The combined alkaline extracts are re-extracted 3 times with 5 ml of benzene:ethyl ether 70:30. The aqueous alkaline phases are then acidified to pH 4.8 and extracted with ethyl ether: pentane 1:1. These organic extracts are combined, washed until neutral with saturated ammonium sulfate solution, dried and evaporated to give 1.38 g of 5c-9β,15S-dihydroxy-16R,20-dimethyl-8,12-diiso-prost-5-en-13-ynoic acid-15-DIOX-ether.

Using the same procedure but starting from the following acetalic ethers, in the form of 3'-THP-ethers and of 3'-DIOX-ethers: 2β-hydroxy-cyclopentyl-1β-acetic acid-γ-lactols:

5α-(2'-bromo-3'R-hydroxy-4'R-methyl-non-1'-trans-1'-enyl);
5α-(2'-bromo-3'S-hydroxy-oct-1'-trans-1'-enyl);
5α-(2'-bromo-3'S-hydroxy-5'-oxa-non-1'-trans-1'-enyl);

5α-(2'-bromo-3'S-hydroxy-4'S-methyl-oct-1'-trans-1'-enyl);

5α-(2'-bromo-3'S-hydroxy-4'S-methyl-non-1'-trans-1'-enyl);

the 15-acetalic ethers (15-THP-ethers, 15-DIOX-ethers) of the following acids were obtained:

5c-9β,15R-dihydroxy-16R,20-dimethyl-8,12-diisoprost-5-en-13-ynoic acid;

5c-9β,15S-dihydroxy-8,12-diiso-prost-5-en-13-ynoic acid;

5c-9β,15S-dihydroxy-8,12-diiso-17-oxa-20-methyl-prost-5-en-13-ynoic acid;

5c-9β,15S-dihydroxy-16S-methyl-8,12-diiso-prost-5-en-13-ynoic acid;

5c-9β,15S-dihydroxy-16S,20-dimethyl-8,12-diiso-prost-5-en-13-ynoic acid.

EXAMPLE 3

A solution of 0.3 g of 5c-9α,15S-dihydroxy-prost-5-en-13-ynoic acid-15-DIOX-ether in 15 ml of ethyl ether is treated with an excess of an ether solution of diazomethane. This is kept for one hour at room temperature and then evaporated under vacuum to yield 0.3 g of 5c-9α,15S-dihydroxy-prost-5-en-13-ynoic acid-methylester-15-DIOX-ether.

EXAMPLE 4

0.42 g of 5c-9β,15S-dihydroxy-17-oxa-20-methyl-8,12-diiso-prost-5-en-13-ynoic acid-n-heptylester-15-THP-ether is obtained by reacting 0.4 g of the free acid in 28 ml of CH$_2$Cl$_2$ and 0.8 ml of pyridine with 0.85 ml of n-heptanol and 0.5 g of dicyclohexylcarbodiimide. After three hours the mixture is chromatographed on silica gel and eluted with cyclohexane:ethyl ether 70:30 to give the ester.

EXAMPLE 5

Using one of the procedures described in examples 3 or 4, by reacting one of the prost-5-en-13-ynoic acids prepared as described in examples 1 and 2, with a diazoalkane (example 3) or with an alcohol in the presence of cyclohexylcarbodiimide (example 4), the corresponding C$_1$–C$_{12}$ alkyl esters are prepared.

EXAMPLE 6

In a solution of 450 mg of 5c-9α,15S-dihydroxy-16R-methyl-prost-5-en-13-ynoic acid-ethyl ester-15-THP-ether and 530 mg of triphenylphosphine in 25 ml of benzene, suspend 400 mg of p-phenylbenzoic acid. While stirring, add dropwise over 15 minutes a solution of 348 mg of ethylazobiscarboxylate in 10 ml of benzene, using external cooling to maintain the temperature at about 10° C. When the acid is completely dissolved, wash the mixture with 0.1 N sulfuric acid, water, 5% sodium bicarbonate and water again, then evaporate to dryness. The residue is chromatographed by thin layer chromatography and eluted with methylenemethyl ether 90:10 to give 0.59 g of 5c-9β,15S-dihydroxy-16R-methyl-prost-5-en-13-ynoic acid ethyl ester-15-THP-ether-9-p-phenylbenzoate.

EXAMPLE 7

148 mg of propionic acid are added to a solution of 430 mg of 5c-9β,15S-dihydroxy-16S,20-dimethyl-8,12-diiso-prost-5-en-13-ynoic acid-15-THP-ether-methylester and 530 mg of triphenylphosphine in anhydrous THF. It is cooled to 0° and a THF solution containing 348 mg of ethyl azobiscarboxylate is added. This is stirred for 15 minutes then evaporated to dryness. The residue is partitioned between ethyl ether: pentane 1:1 and water and the organic phase washed with dilute acid, water, sodium bicarbonate and water again. It is dried and evaporated to dryness. The residue is chromatographed on 20 g of silica gel, eluted with cyclohexane:ether 75:25 to give 452 mg of 5c-9α,15S-dihydroxy-(16S,20-dimethyl-8,12-diiso-prost-5-en-13-ynoic acid-15-THP-ether-9-propionate methyl ester.

EXAMPLE 8

Using the procedures described in examples 6 and 7 for reacting one of the carboxylic esters prepared as described in examples 3 to 5, starting with the 13-ynoic acid-15-acetalic ethers prepared as shown in examples 1 and 2 and reaction with triphenylphosphine in benzene and/or tetrahydrofuran and with one of the following carboxylic acids: formic, acetic, propionic, butyric, benzoic, phenylacetic, p-phenylbenzoic and with ethyl azo-biscarboxylate, give the inverted 9-esters (9-formate, 9-acetate, 9-propionate, 9-benzoate, 9-phenyl-acetate, 9-p-phenylbenzoate) of the following compounds, as the 15-bis-acetalic ethers (15-S'-THP, 15-2'-DIOX, 15-4'-methoxy-4'-THP-, 15-3'-methoxy-3'-THP):

5c-9β,15S-dihydroxy-16R-methyl-prost-5-en-13-ynoic acid;

5c-9β,15S-dihydroxy-prost-5-en-13-ynoic acid;

5c-9β,15S-dihydroxy-20-methyl-prost-5-en-13-ynoic acid;

5c-9β,15S-dihydroxy-20-ethyl-prost-5-en-13-ynoic acid;

5c-9β,15S-dihydroxy-16S-methyl-prost-5-en-13-ynoic acid;

5c-9β,15S-dihydroxy-16R,20-dimethyl-prost-5-en-13-ynoic acid;

5c-9β,15S-dihydroxy-17-cyclohexyl-16R-methyl-18,19,20-trinor-prost-5-en-13-ynoic acid;

5c-9β,15S-dihydroxy-17-oxa-prost-5-en-13-ynoic acid;

5c-9β,15S-dihydroxy-17-oxa-20-methyl-prost-5-en-13-ynoic acid;

5c-9β,15S-dihydroxy-17-oxa-16R-methyl-prost-5-en-13-ynoic acid;

5c-9β,15S-dihydroxy-17-oxa-16S-methyl-prost-5-en-13-ynoic acid;

5c-9β,15S-dihydroxy-17-cyclopentyl-18,19,20-trinor-prost-5-en-13-ynoic acid;

5c-9β,15S-dihydroxy-17-cyclohexyl-18,19,20-trinor-prost-5-en-13-ynoic acid;

5c-9β,15S-dihydroxy-17-p-chlorophenyl-18,19,20-trinor-prost-5-en-13-ynoic acid;

5c-9β,15S-dihydroxy-17-phenyl-18,19,20-trinor-prost-5-en-13-ynoic acid;

5c-9β,15S-dihydroxy-16-cyclohexyloxy-17,18,19,20-tetranor-prost-5-en-13-ynoic acid;

5c-9β,15S-dihydroxy-16-phenoxy-17,18,19,20-tetranor-prost-5-en-13-ynoic acid;

5c-9α,15S-dihydroxy-16R,20-dimethyl-8,12-diiso-prost-5-en-13-ynoic acid;

5c-9α,15S-dihydroxy-8,12-diiso-prost-5-en-13-ynoic acid;

5c-9α,15S-dihydroxy-17-oxa-20-methyl-8,12-diiso-prost-5-en-13-ynoic acid;

5c-9α,15S-dihydroxy-16S,20-dimethyl-8,12-diiso-prost-5-en-13-ynoic acid;

5c-9α,15S-dihydroxy-16S-methyl-8,12-diiso-prost-5-en-13-ynoic acid;

5c-9α,15S-dihydroxy-17-cyclohexyl-18,19,20-trinor-8,12-diiso-prost-5-en-13-ynoic acid;

in the form of the $C_1$–$C_{12}$ alkyl esters, preferably methyl and ethyl. All of these compounds are oils whose IR spectra indicate the absence of any bands attributable to free hydroxyl.

EXAMPLE 9

To a solution of a 15-acetalic ether from those listed in example 8, for example 5c-9β,15S-dihydroxy16R-methyl-prost-5-en-13-ynoic acid-methyl ester-15S-tetrahydropyranylether-9-p-phenylbenzoate (0.4 g) in 20 ml of acetone is added 15 ml of 0.15 N oxalic acid and the mixture is refluxed for 45 minutes. The solvent is evaporated off under vacuum and the aqueous solution is extracted with ethyl ether, which is washed with saturated ammonium sulfate solution, dried and evaporated to dryness. The residue is purified by silica gel chromatography (eluted with cyclohexane-ethyl ether) to give 0.32 g of 5c-9β,15S-dihydroxy-16R-methyl-prost-5-en-13-ynoic acid methyl ester-9-p-phenylbenzoate.

By this procedure, one can obtain the 9-inverted ester 15-free alcohols of the prost-5-en-13-ynoic acids described in example 8.

EXAMPLE 10

A solution of a diester from among those in example 9, for instance, 5c-9β,15S-dihydroxy-16R-methyl-prost-5-en-13-ynoic acid-methyl ester-9-p-phenylbenzoate (0.32 g) in an anhydrous alcohol (that which corresponds to the carboxyl ester), for example methanol, is treated at room temperature with 1.2 equivalents of anhydrous potassium carbonate (98 mg). After two hours the reaction is complete and the mixture is neutralized with 15% acetic acid in methanol and evaporated to dryness. The residue is taken up in ethyl ether, which is then washed until neutral, dried and evaporated to dryness. The residue is purified by silica gel chromatography, eluted wth methylene chloride-ethyl ether, to give 0.195 g of 5c-9β,15S-dihydroxy-16R-methyl-prost-5-en-13-ynoic acid-methyl ester. A solution of 0.1 g of this compound in 3 ml of methanol has added to it 0.5 ml of 10% aqueous $K_2CO_3$, and it refluxed for 30 minutes. The solvent is evaporated off under vacuum and the residue diluted with water, then extracted with ether and the ether extracts discarded. The aqueous solution is acidified to pH 4.8, extracted with ether and the organic phase washed until neutral, dried and evaporated to dryness to yield 0.09 g of 5c-9β,15S-dihydroxy-16R-methyl-prost-5-en-13-ynoic acid.

EXAMPLE 11

15 ml of 0.15 N oxalic acid is added to a solution of 0.45 g of 5c-9α,15S-dihydroxy-16S,20-dimethyl-8,12-diiso-prost-5-en-13-ynoic acid-15-THP-ether-9-propionate in 20 ml of acetone. After 5 hours at 40° C. the acetone is evaporated and the residue extracted with ether to give 0.36 g of 5c-9α,15S-dihydroxy-16S,20-dimethyl-8,12-diiso-prost-5-en-13-ynoic acid-methyl ester-9-propionate.

A solution of this compound in 20 ml of MeOH is refluxed for one hour with 5 ml of 10% aqueous $K_2CO_3$. The methanol is evaporated off, the residue extracted with ethyl ether and these extracts discarded. The aqueous solution is acidified to pH 4.8 and saturated with ammonium sulfate, then extracted with ether. The combined ether extracts are dried and evaporated to dryness to give 0.27 g of pure 5c-9α,15S-dihydroxy-16S,20-dimethyl-8,12-diiso-prost-5-en-13-ynoic acid.

EXAMPLE 12

Proceeding as described in example 11, and starting from the 15-acetalic-9-esters of the prost-5-en-13-ynoic acid carboxylic esters, the 15 -hydroxy-9,15-dihydroxy-carboxylic esters and the corresponding free acids of the following compounds are obtained in the form of their $C_1$–$C_{12}$ alkyl esters, preferably methyl and ethyl:

5c-9β,15S-dihydroxy-16R-methyl-prost-5-en-13-ynoic acid;
5c-9β,15S-dihydroxy-prost-5-en-13-ynoic acid;
5c-9β,15S-dihydroxy-20-methyl-prost-5-en-13-ynoic acid;
5c-9β,15S-dihydroxy-20-ethyl-prost-5-en-13-ynoic acid;
5c-9β,15S-dihydroxy-16S-methyl-prost-5-en-13-ynoic acid;
5c-9β,15S-dihydroxy-16R,20-dimethyl-prost-5-en-13-ynoic acid;
5c-9β,15S-dihydroxy-17-cyclohexyl-16R-methyl-18,19,20-trinor-prost-5-en-13-ynoic acid;
5c-9β,15S-dihydroxy-17-oxa-prost-5-en-13-ynoic acid;
5c-9β,15S-dihydroxy-17-oxa-20-methyl-prost-5-en-13-ynoic acid;
5c-9β,15S-dihydroxy-17-oxa-16R-methyl-prost-5-en-13-ynoic acid;
5c-9β,15S-dihydroxy-17-oxa-16S-methyl-prost-5-en-13-ynoic acid;
5c-9β,15S-dihydroxy-17-cyclopentyl-18,19,20-trinor-prost-5-en-13-ynoic acid;
5c-9β,15S-dihydroxy-17-cyclohexyl-18,19,20-trinor-prost-5-en-13-ynoic acid;
5c-9β,15S-dihydroxy-17-p-chlorophenyl-18,19,20-trinor-prost-5-en-13-ynoic acid;
5c-9β,15S-dihydroxy-17-phenyl-18,19,20-trinor-prost-5-en-13-ynoic acid;
5c-9β,15S-dihydroxy-16-cyclohexyloxy-17,18,19,20-tetranor-prost-5-en-13-ynoic acid;
5c-9β,15S-dihydroxy-16-phenoxy-17,18,19,20-tetranor-prost-5-en-13-ynoic acid;
5c-9β,15S-dihydroxy-16R,20-dimethyl-8,12-diiso-prost-5-en-13-ynoic acid;
5c-9β,15R-dihydroxy-16R,20-dimethyl-8,12-diiso-prost-5-en-13-ynoic acid;
5c-9α,15S-dihydroxy-8,12-diiso-prost-5-en-13-ynoic acid;
5c-9α,15S-dihydroxy-17-oxa-20-methyl-8,12-diiso-prost-5-en-13-ynoic acid;
5c-9α,15S-dihydroxy-16S,20-dimethyl-8,12-diiso-prost-5-en-13-ynoic acid;
5c-9α,15S-dihydroxy-16S-methyl-8,12-diiso-prost-5-en-13-ynoic acid;
5c-9α,15S-dihydroxy-17-cyclohexyl-18,19,20-trinor-8,12-diiso-prost-5-en-13-ynoic acid.

EXAMPLE 13

An acetalic ether such as those in example 8, for instance 5c-9β,15S-dihydroxy-17-oxa-prost-5-en-13-ynoic acid-methyl-ester-15-THP-ether-9benzoate (0.45 g) is refluxed for 2 hours in 25 ml of 5% $K_2CO_3$ in MeOH:$H_2O$ 80:20. It is evaporated under vacuum, the residue taken up in water which is then extracted with ethyl ether and the organic phase discarded. The aqueous solution is acidified to pH 4.8 and extracted 3 times with 10 ml of ethyl ether each time. The organic phases are combined, washed until neutral with saturated ammonium sulfate solution, dried and evaporated to dryness to yield 0.32 g of 5c-9β,15S-dihydroxy-17-oxaprost-5-en-13-ynoic acid-15-THP-ether.

EXAMPLE 14

Starting with 0.32 g of 5c-9α,15S-dihydroxy-16S,20-dimethyl-8,12-diiso-prost-5-en-13-ynoic acid-15-THP-ether-9propionate methyl ester, after treatment with 1.2 equivalents an anhydrous $K_2CO_3$ in anhydrous methanol for two hours at room temperature, neutralization with saturated $NaH_2PO_4$, evaporation of the solvent and extraction with ether one obtains 0.29 g of 5c-9α,16S-dihydroxy-16S,20-dimethyl-8,12-diiso-prost-5-en-13-ynoic acid-15-THP-ether-methylester.

EXAMPLE 15

Using the procedure described in examples 13 and 14 and starting from a 15-acetalic-9-ester among those in example 8, the corresponding 15-acetalic-prost-5-en-13-ynoic acid-9-hydroxy derivatives are obtained as the free carboxylic acids or as esters.

By deacetalization, the corresponding 9,15-hydroxy derivatives are obtained.

EXAMPLE 16

0.9 g of 5c-9α,15S-dihydroxy-16S,20-dimethyl-prost-5-en-13-ynoic acid-methylester-15-THP-ether in 10 ml of benzene:DMSO 75:25 are treated with 1.25 g of dicyclohexylcarbodiimide and 1.95 ml of a solution of pyridine trifluoroacetate (made by diluting 1 ml of trifluoroacetic acid and 2 ml of pyridine to 25 ml with benzene:DMSO 75:25). This is stirred for 3 hours and then a solution of 0.55 g of oxalic acid dihydrate in MeOH is added and the reaction mixture diluted with 10 ml of water. The precipitate is filtered off and the organic phase is separated, evaporated to dryness then treated with 15 ml of acetone and 10 ml of 0.15 N oxalic acid for 6 hours at 30° C. The acetone is distilled off under vacuum and the residue extracted with ethyl ether. The ethyl ether is evaporated to dryness and the residue chromatographed on silica gel, eluted with $CH_2Cl_2$-ethyl ether, yielding 0.71 g of 5c-9-oxo-15S-hydroxy-16S,20-dimethyl-8,12-diiso-prost-5-en-13-ynoic acid methylester.

EXAMPLE 17

0.25 g of 5c-9β,15S-dihydroxy-17-oxa-prost-5-en-13-ynoic acid-15-THP-ether in 10 ml of acetone is cooled to −15° C. and 0.5 ml of Jones reagent is added. The reaction mixture is maintained at −10°–12° C. for 30 minutes. It is then diluted with 40 ml of benzene, washed repeatedly with saturated ammonium sulfate solution until neutral and evaporated to dryness. The crude reaction product is dissolved in 20 ml of acetone and 20 ml of 0.2 N oxalic acid is added, and the mixture left at 10° C. for 6 hours. The acetone is evaporated off under vacuum and the aqueous phase extracted with ether. The combined ether extracts are washed to neutral and then evaporated. The residue is chromatographed on silica gel, eluted with methylene chloride-ethyl ether, yielding 0.12 g of 5c-9-oxo-15S-hydroxy-17-oxa-prost-5-en-13-ynoic acid.

EXAMPLE 18

Using the procedures of examples 16 and 17 and starting from the 15-acetals of the 9α,15S; 9β,15S; 9α,15R and 9β,15R-prost-5-en-13-ynoic acids listed in example 1 to 15, either in free acid form or as esters, oxidation with Jones reagent in acetone or with dicyclohexylcarbodiimide in benzene-DMSO and successive deacetalization yielded the free acids or the esters of the following 9-oxo-derivatives:

5c-9-oxo-15S-hydroxy-16R-methyl-prost-5-en-13-ynoic acid;
5c-9-oxo-15S-hydroxy-20-methyl-prost-5-en-13-ynoic acid;
5c-9-oxo-15S-hydroxy-16S-methyl-prost-5-en-13-ynoic acid;
5c-9-oxo-15S-hydroxy-16R,20-dimethyl-prost-5-en-13-ynoic acid;
5c-9-oxo-15S-hydroxy-16R-methyl-18,19,20-trinor-17-cyclohexyl-prost-5-en-13-ynoic acid;
5c-9 -oxo-15S-hydroxy-20-ethyl-prost-5-en-13-ynoic acid;
5c-9-oxo-15S-hydroxy-17-oxa-prost-5-en-13-ynoic acid;
5c-9-oxo-15S-hydroxy-17-oxa-20-methyl-prost-5-en-13-ynoic acid;
5c-9-oxo-15S-hydroxy-17-oxa-16R-methyl-prost-5-en-13-ynoic acid;
5c-9-oxo-15S-hydroxy-17-oxa-16S-methyl-prost-5-en-13-ynoic acid;
5c-9-oxo-15S-hydroxy-18,19,20-trinor-17-cyclopentyl-prost-5-en-13-ynoic acid;
5c-9-oxo-15S-hydroxy-18,19,20-trinor-17-cyclohexyl-prost-5-en-13-ynoic acid;
5c-9-oxo-15S-hydroxy-18,19,20-trinor-17p-chlorophenyl-prost-5-en-13-ynoic acid;
5c-9-oxo-15S-hydroxy-18,19,20-trinor-17-phenyl-prost-5-en-13-ynoic acid;
5c-9-oxo-15S-hydroxy-17,18,19,20-tetranor-16-cyclohexyloxy-prost-5-en-13-ynoic acid;
5c-9-oxo-15S-hydroxy-17,18,19,20-tetranor-16-phenoxy-prost-5-en-13-ynoic acid;

EXAMPLE 19

0.23 g of 5c-9α,15S-dihydroxy-16S,20-dimethyl-8,12-diiso-prost-5-en-13-ynoic acid-15-THP-ether methyl ester is dissolved in 2.5 ml of benzene:DMSO (75:25) and stirred at room temperature while 0.32 g of dicyclohexylcarbodiimide and then 0.48 ml of a solution of pyridine trifluoroacetate in benzene-DMSO (75:25) are added. Stirring is continued for 3 hours and then a solution of 130 mg of oxalic acid dihydrate in 0.75 ml of methanol is added, followed by 3 ml of water and 10 ml of benzene. Filter, separate off the organic layer and re-extract the water phase with benzene. Combine the organic phases and wash to neutrality and then evaporate to dryness. The yield is 0.22 g of 5c-9-oxo-15S-hydroxy-16S,20-dimethyl-8,12-diiso-prost-5-en-13-ynoic acid-15-THP-ether methylester. This compound is dissolved in 10 ml of acetone and added to 8 ml of 0.25N citric acid. This is maintained for 6 hours at 40° C., concentrated under vacuum and extracted with ether. The organic phase is evaporated and the residue chromatographed in 1.2 g of silica gel, eluted with methylene chloride-ether, to give 0.14 g of 5c-9-oxo-15S-hydroxy-16S,20-dimethyl-8,12-diiso-prost-5-en-13-ynoic acid methylester.

EXAMPLE 20

A solution of 0.49 g of 5c-9β,15S-dihydroxy-16R-methyl-17-cyclohexyl-18,19,20-trinor-8,12-diiso-prost-5-en-13-ynoic acid-15-THP-ether in 20 ml of acetone is cooled to −20° C. To this is added 0.82 ml of Jones reagent. After one hour at −12° to −10° C., this is diluted with 80 ml of benzene and washed until neutral with saturated ammonium sulfate solution. The organic phase is dried and evaporated to dryness, the residue dissolved in 20 ml of acetone and 15 ml of 0.09 N oxalic acid is added. This is left overnight at +40° C., then the solvent is evaporated off under vacuum and the residue extracted with ether. The combined organic extracts are evaporated to dryness and the residue purified by silica gel chromatography, to give 0.31 g of 5c-9-oxo-15S-hydroxy-16R-methyl-17-cyclohexyl-18,19,20-trinor-8,12-diiso-prost-5-en-13-ynoic acid.

EXAMPLE 21

Using the procedure described in examples 19 and 20 for oxidation of the 15-acetalic-9,15-diol-8,12-diiso-prost-5-en-13-ynoic acids of examples 2, 4, 8 and 15 and following deacetalization we prepared either in the form of free acids or of their esters, the following 9-oxo-8,12-diiso-prost-5-en-13-ynoic acids;

5c-9-oxo-15S-hydroxy-16R,20-dimethyl-8,12-diiso-prost-5-en-13-ynoic acid;
5c-9-oxo-15R-hydroxy-16R,20-dimethyl-8,12-diiso-prost-5-en-13-ynoic acid;
5c-9-oxo-15S-hydroxy-8,12-diiso-prost-5-en-13-ynoic acid;
5c-9-oxo-15S-hydroxy-17-oxa-20-methyl-8,12-diiso-prost-5-en-13-ynoic acid;
5c-9-oxo-15S-hydroxy-16S-methyl-8,12-diiso-prost-5-en-13-ynoic acid;
5c-9-oxo-15S-hydroxy-16S,20-dimethyl-8,12-diiso-prost-5-en-13-ynoic acid.

EXAMPLE 22

A solution of 0.32 g of 5c-9α,15S-dihydroxy-16R-methyl-prost-5-en-13-ynoic acid-15-(4'-methoxy-4'-THP-ether) in 20 ml of acetone is treated at 38° C. for 4 and 1 half hours with 15 ml of 0.15 N oxalic acid. The solvent is distilled off under vacuum, the aqueous phase extracted with methylenechloride and the organic phases combined and washed to neutrality and then concentrated to a small volume for chromatography on 1.8 g of silica gel, eluted with methylene-chloride-ethyl acetate, to give 0.22 g of 5c-9α,15S-dihydroxy-16R-methyl-prost-5-en-13-ynoic acid.

EXAMPLE 23

0.22 g of 5c-9β,15S-dihydroxy-8,12-diiso-prost-5-en-13-ynoic acid-15-DIOX-ether-n-pentyl-ester in 10 ml of acetone is treated at 40° C. with 6 ml of 0.1 N oxalic acid. The solvent is evaporated off and the aqueous phase extracted with ether. The ether extracts are evaporated to dryness and purified by chromatography on silica gel (1.2 g) eluting with CH₂Cl₂-ethyl ether to give 0.14 g of 5c-9β,15S-dihydroxy-8,12-diiso-prost-5-en-13-ynoic acid-n-pentyl ester.

EXAMPLE 24

Using the procedures in examples 22 and 23 for deacetalization of the acetalic 9,15-dihydroxy-prost-5-en-13-ynoic acids listed in examples 1 to 5, as either free acids or their esters, one obtains the following prost-13-ynoic acids, either free or esterified:

5c-9α,15S-dihydroxy-16R-methyl-prost-5-en-13-ynoic acid;
5c-9α,15S-dihydroxy-20-methyl-prost-5-en-13-ynoic acid;
5c-9α,15S-dihydroxy-16S-methyl-prost-5-en-13-ynoic acid;
5c-9α,15S-dihydroxy-16R,20-dimethyl-prost-5-en-13-ynoic acid;
5c-9α,15S-dihydroxy-16R-methyl-18,19,20-trinor-17-cyclohexyl-prost-5-en-13-ynoic acid;
5c-9α,15S-dihydroxy-18,19,20-trinor-17-cyclopentyl-prost-5-en-13-ynoic acid;
5c-9α,15S-dihydroxy-18,19,20-trinor-17-cyclohexyl-prost-5-en-13-ynoic acid;
5c-9α,15S-dihydroxy-18,19,20-trinor-17-p-chlorophenyl-prost-5-en-13-ynoic acid;
5c-9α,15S-dihydroxy-18,19,20-trinor-17-phenyl-prost-5-en-13-ynoic acid;
5c-9α,15S-dihydroxy-17,18,19,20-tetranor-16-cyclohexyloxy-prost-5-en-13-ynoic acid;
5c-9α,15S-dihydroxy-17,18,19,20-tetranor-16-phenoxy-prost-5-en-13-ynoic acid;
5c-9α,15S-dihydroxy-20-ethyl-prost-5-en-13-ynoic acid;
5c-9α,15S-dihydroxy-17-oxa-prost-5-en-13-ynoic acid;
5c-9α,15S-dihydroxy-17-oxa-20-methyl-prost-5-en-13-ynoic acid;
5c-9α,15S-dihydroxy-17-oxa-16R-methyl-prost-5-en-13-ynoic acid;
5c-9α,15S-dihydroxy-17-oxa-16S-methyl-prost-5-en-13-ynoic acid;
5c-9β,15S-dihydroxy-16R,20-dimethyl-8,12-diiso-prost-5-en-13-ynoic acid;
5c-9β,15R-dihydroxy-16R,20-dimethyl-8,12-diiso-prost-5-en-13-ynoic acid;
5c-9β,15S-dihydroxy-8,12-diiso-prost-5-en-13-ynoic acid;
5c-9β,15S-dihydroxy-17-oxa-20-methyl-8,12-diiso-prost-5-en-13-ynoic acid;
5c-9β,15S-dihydroxy-16S-methyl-8,12-diiso-prost-5-en-13-ynoic acid;
5c-9β,15S-dihydroxy-16S,20-dimethyl-8,12-diiso-prost-5-en-13-ynoic acid.

EXAMPLE 25

A stirred solution of 5 g of 5α-hydroxymethyl-(3'-methoxy-3'-THP-ether)-cyclopentan-2β,4α-dihydroxy-1β-acetic acid-γ-lactone in 15 ml of pyridine is treated with 4.2 g of p-toluene-sulfonyl chloride. This is maintained for 12 hours at room temperature, then diluted with water and ice and extracted with ethyl ether. The organic extracts are washed with a 30% aqueous solution of citric acid, 10% sodium bicarbonate and water until neutral, dried and evaporated to dryness, to give 6.9 g of 5α-hydroxymethyl-(3'-methoxy-3'-THP-ether)-cyclopentan-2β,4β-dihydroxy-1β-acetic acid-γ-lactone-4-p-toluenesulfonate. A solution of this compound in anhydrous ethyl ether is combined with a solution of MgI₂ is anhydrous ethyl ether (prepared by adding to a suspension of 2.46 g of magnesium, in 200 ml of anhydrous ether, 25.4 g of iodine, bit by bit, until it is all in solution). After this has been added to the tosylate, the mixture is stirred for 1 hour and 30 minutes and then decomposed by careful addition of water and ice with forceful mixing. The organic phase is separated off and the aqueous phase re-extracted. The combined organic extracts are evaporated to dryness to give a mixture of 5α-hydroxy-methyl-(3'-methoxy-3'-THP-ether)-cyclopentan-2β-hydroxy-1β-acetic acid-γ-lactone-4α-iodide and the free 5α-hydroxy-methyl alcohol. The two compounds can be separated by silica gel chromatography, with elution by cyclohexane-methylene chloride 20:80. The mixture is dissolved in benzene and 0.8 molar equivalents of 3-methoxy-2,3-dihydro-4H-pyran and 0.08 molar equivalents of p-toluene-sulfonic acid are added. This is maintained for 3 hours at room temperature, then washed with 10% sodium bicarbonate, and water until neutral, then evaporated to dryness to give 5.3 g of 5α-hydroxymethyl-(3'-methoxy-3'-THP-ether)-4α-iodo-2β-hydroxy-cyclopentan-1β-acetic acid-γ-lactone. This product is dissolved in benzene and treated at 50° with 1.6 molar equivalents of tributyltin hydride, under nitrogen. After 12 hours, the benzene phase is washed repeatedly with a 10% solution of sodium and potassium tartrate, the organic phase is evaporated to dryness and the residue of crude 5α-hydroxymethyl-(3'-methoxy-3'-THP-ether)-2β-hydroxy-cyclopentan-1β-acetic acid-γ-lactone is dissolved in 50 ml of acetone and treated overnight at room temperature with 15 ml of 1N $H_2SO_4$. The acetone is evaporated off under vacuum, the aqueous phase is saturated with ammonium sulfate and extracted with ethyl ether. The organic phases are washed to neutrality, evaporated to dryness, and purified by silica gel chromatography, with methylene chloride as eluent, giving 1.93 g of 5α-hydroxymethyl-cyclopentan-2β-hydroxy-1β-acetic acid-γ-lactone, m.p. 50°–52° C.

EXAMPLE 26

A solution of 7.95 g of 5α-methoxymethyl-2β-hydroxy-cyclopent-3(1)-en-1β-acetic acid-γ-lactone in 290 ml of methanol is refluxed with a solution of 26.25 g of potassium carbonate in 33 ml of water until the γ-lactone group is completely saponified. After cooling, 1 g of $PtO_2$ is added and hydrogenation at normal pressure is continued until 1 molar equivalent of hydrogen has been taken up. The catalyst is filtered out, the reaction mixture is acidified to pH 3 and let stand for 3 hours at room temperature. The solvent is evaporated off, the residue extracted with ethyl ether, which is then washed until neutral and evaporated to dryness, to yield 7.5 g of 5α-methoxymethyl-2β-hydroxy-cyclopent-1 β-acetic acid-γ-lactone, $[α]_D = +14.8°$; $[α]_{365°} = +66.4°$ ($CHCl_3$).

Using the same working conditions, starting from 5α-benzyloxy-methyl-9β-hydroxy-cyclopent-3(4)-en-1β-acetic acid-γ-lactone and from 5β-methoxymethyl and 5β-benzyloxymethyl-2α-hydroxy-cyclopent-3(4)-en-1α-acetic acid -γ-lactone, one obtains: 5α-benzyloxymethyl-23-hydroxy-cyclopentan-1β-acetic acid-γ-lactone; 5β-benzyloxymethyl-2α-hydroxy-cyclopentan-1α-acetic acid-γ-lactone; 5α-methoxymethyl-2α-hydroxy-cyclopentan-1α-acetic acid-γ-lactone.

EXAMPLE 27

7.5 g of 5α-methoxymethyl-2β-hydroxy-cyclopentan-1β-acetic acid-γ-lactone are dissolved in 300 ml of methylene chloride. Under a nitrogen atmosphere, and at −70° C. over a period of 10 minutes, 10.4 ml of a solution of boron tribromide in methylene chloride is added. After standing for 20 minutes at −70° C., the temperature is allowed to rise to 0° C., where it is maintained for one hour, and then to room temperature, where it is left to sit for 3 hours. The excess reagent is decomposed with water and ice, the organic phase is separated off and the aqueous phase re-extracted with chloroform. The combined organic phases are washed repeatedly with saturated sodium bicarbonate solution, then with water, dried on $Na_2SO_4$ and evaporated to dryness to give 6.18 g of 5α-hydroxymethyl-2β-hydroxy-cyclopentan-1β-acetic acid-γ-lactone, m.p. 52°–53° C.; $[α]_D = +27.3°$, $[α]_{365°} = +110°$ ($CHCl_3$). Using the same procedure and starting from the compounds listed in example 26, one prepares the 5β-hydroxymethyl-2α-hydroxy-cyclopentan-1α-acetic acid-γ-lactone, m.p. 50°–51°; $[α]_D = −26°$; $[α]_{365°} = −110°$ ($CHCl_3$).

EXAMPLE 28

13.2 g of 2α,4α-dihydroxy-5β-hydroxymethyl-DIOX-ether)-cyclopentan-1α-acetic acid-γ-lactone are reacted in 26 ml of pyridine with 1.15 molar equivalents of p-toluene-sulfonyl chloride, to give the 2α,4α-dihydroxy-5β-(hydroxymethyl-DIOX-ether)-cyclopentan-1α-acetic acid-γ-lactone-4-p-toluene-sulfonate. A solution of this product in anhydrous ethyl ether is cooled to 0°–2° C. and 10 molar equivalents of $MgI_2$ in anhydrous ethyl ether are added. The mixture is stirred for one hour and then hydrolyzed with water and ice to obtain a mixture of the 5α-hydroxymethyl alcohol and the oxanylether, which is then dissolved in 30 ml of acetone. 8 ml of 1 N $H_2SO_4$ are added. The solvent is evaporated off and the aqueous layer extracted with ethyl acetate to give 12.8 g of 2α-hydroxy-5β-hydroxymethyl-4β-iodo-cyclopentan-1α-acetic acid-γ-lactone. This compound is dissolved in anhydrous benzene and 1.6 molar equivalents of tributyl-tin hydride and 0.2 g of azobisisobutyronitrile added, and then the reaction is allowed to proceed at 55° for 18 hours. The reaction mixture is evaporated to dryness and chromatographed on silica gel, to yield 6.8 g of 2α-hydroxy-5β-hydroxymethyl-cyclopentan-1α-acetic acid-γ-lactone.

EXAMPLE 29

4.7 g of 5β-hydroxymethyl-2α-hydroxy-cyclopentan-1α-acetic acid-γ-lactone in 112 ml of benzene and 37 ml of anhydrous DMSO is combined with 18.75 g of dicyclohexylcarbodiimide and 28.9 ml of a solution of pyridine trifluoroacetate in DMSO. After stirring for 3 hours, add drop by drop 8.2 g of oxalic acid dihydrate in 45 ml of methanol, then dilute with 100 ml of water and 200 ml of benzene. The precipitate of dicyclohexylurea is filtered off, the organic phase is separated and the water phase is repeatedly washed with benzene. The combined organic phases are washed to neutrality and evaporated to dryness, to yield 4.62 g of 5β-formyl-2α-hydroxy-cyclopentan-1α-acetic acid-γ-lactone. In the same way, starting from 5α-hydroxy-methyl-2β-hydroxy-cyclopentan-1β-acetic acid-γ-lactone, the 5α-formyl-2β-hydroxy-cyclopentan-1β-acetic acid-γ-lactone is prepared. Both of these aldehydes are used without further purification.

EXAMPLE 30

With stirring, under an inert gas atmosphere, to a suspension of 0.96 g of an 80% dispersion of NaH mineral oil in 120 ml of anhydrous dimethoxyethane a solution of 7.76 g of (2-oxo-3R-methyl-heptyl)-dimethoxyphosphonate in 120 ml of dimethoxyethane is added drop by drop. Stirring is continued until no more hydrogen is evolved. After one hour, add 5.91 g of N-bromosuccinimide and continue to stir for 15 minutes longer. Add all at one time a solution of 3.12 g of 5β-formyl-2α-hydroxy-cyclopentan-1β-acetic acid-γ-lactone, and stir for one hour. Neutralize by addition of a saturated solution of $NaH_2PO_4$, dilute with benzene, separate the aqueous phase and re-extract with more benzene. The combined organic phases are dried and evaporated to dryness. The residue is chromatographed on silica gel with cyclohexane-methylene chloride 80–20, to give 6.76 g of 2α-hydroxy-cyclopentan-1α-acetic acid-γ-lactone-5β-(2'-bromo-3'-oxo-4'-R-methyl-oct-1'-trans-1'-enyl).

EXAMPLE 31

In the procedure of example 30, when N-bromo-acetamide is used instead of the N-bromo-succinimide and (2-oxo-3(S,R)-methyl-4-oxa-octyl)-dimethoxy phosphonate for the other phosphonate, one obtains the carbanion of (1-bromo-2-oxo-3(S,R)-methyl-4-oxa-octyl)-dimethoxyphosphonate, and then by reacting with the 5β-formyl derivative, one prepares the 2α-hydroxy-cyclopentan-1α-acetic acid-γ-lactone-5β-(2'-bromo-3'-oxo-3'(S,R)-methyl-5'-oxa-non-1'-trans-1'-enyl).

EXAMPLE 32

In the procedure of example 30, if N-bromo-caprolactam is used instead of N-bromo-succinimide and the phosphonate used is the (2-oxo-octyl)-dimethoxy phosphonate, the carbanion obtained is that of (1-bromo-2-oxo-octyl)-dimethoxy phosphonate, which reacts with 2β-hydroxy-cyclo-pentan-1β-acetic acid-γ-lactone-5α-formyl to give the 2β-hydroxy-cyclopentan-1β-acetic acid-γ-lactone-5α-(2'-bromo-3'-oxo-non-1'-trans-1'-enyl).

EXAMPLE 33

Using in the procedures described in examples 30 and 32 a halogen imide chosen from the group N-bromo-succinimide, N-bromo-acetamide and N-bromo-caprolactam and reacting these with the carbanion of the corresponding non-halogenated phosphonates, one obtains in situ the carbanion of the following halogenated phosphonates:

(1-bromo-2-oxo-3R -methyl-heptyl)-dimethoxy phosphonate;
(1-bromo-2-oxo-heptyl)-dimethoxy phosphonate;
(1-bromo-2-oxo-octyl)-dimethoxy phosphonate;
(1-bromo-2-oxo-3S-methyl-heptyl)-dimethoxy phosphonate;
(1-bromo-2-oxo-3-oxo-3R-methyl-octyl)-dimethoxy phosphonate;
(1-bromo-2-oxo-3R-methyl-4-cyclohexyl-butyl)-dimethoxy phosphonate;
(1-bromo-2-oxo-nonyl)-dimethoxy phosphonate;
(1-bromo-2-oxo-4-oxa-heptyl)-dimethoxy phosphonate;
(1-bromo-2-oxo-4-oxa-octyl)-dimethoxy phosphonate;
(1-bromo-2oxo-3R-methyl-4-oxa-heptyl)-dimethoxyphosphonate;
(1-bromo-2-oxo-3S-methyl-4-oxa-octyl)-dimethoxy phosphonate;
(1-bromo-2-oxo-4-cyclopentyl-butyl)-dimethoxy phosphonate;
(1-bromo-2-oxo-4-cyclohexyl-butyl)-dimethoxy phosphonate;
(1-bromo-2-oxo-4-p-chlorophenyl-butyl)-dimethoxy phosphonate;
(1-bromo-2-oxo-4-phenyl-butyl)-dimethoxy phosphonate;
(1-bromo-2-oxo-4-cyclohexyloxy-butyl)-dimethoxy phosphonate;
(1-bromo-2-oxo-4-phenoxy-butyl)-dimethoxy phosphonate;

which, when reacted with one of the two aldehydes 2α-hydroxy-cyclopentan-1α-acetic acid-γ-lactone-5β-formyl or 2β-hydroxy-cyclopentan-1β-acetic acid-γ-lactone-5α-formyl, prepared as described in example 29, give the following α-halogen-α, β-trans-enones:

2α-hydroxy-cyclopentan-1α-acetic acid-γ-lactones:

5β-(2'-bromo-3'-oxo-oct-1'-trans-1'-enyl);
5β-(2'-bromo-3'-oxo-non-1'-trans-1'-enyl);
5β-(2'-bromo-3'-oxo-doc-1'-trans-1'-enyl);
5β-(2'-bromo-3'-oxo-4'R-methyl-oct-1'-trans-1'-enyl);
5β-(2'-bromo-3'-oxo-4'S-methyl-oct-1'-trans-1'-enyl);
5β-(2'-bromo-3'-oxo-4'R-methyl-non-1'-trans-1'-enyl);
5β-(2'-bromo-3'-oxo-5'-oxa-oct-1'-trans-1'-enyl);
5β-(2'-bromo-3'-oxo-5'-oxa-non-1'-trans-1'-enyl);
5β-(2'-bromo-3'-oxo-4'R-methyl-5'-oxa-oct-1'-trans-1'-enyl);
5β-(2'-bromo-3'-oxo-5'-cyclopentyl-pent-1'-trans-1'-enyl);
5β-(2'-bromo-3'-oxo-5'-cyclohexyl-pent-1'-trans-1'-enyl);
5β-(2'-bromo-3'-oxo-5'-phenyl-pent-1'-trans-1'-enyl);
5β-(2'-bromo-3'-oxo-5'-p-chlorophenyl-pent-1'-trans-1'-enyl);
5β-(2'-bromo-3'-oxo-5'-cyclohexyl-pent-1'-trans-1'-enyl);
5β-(2'-bromo-3'-oxo-5'-phenoxy-pent-1'-trans-1'-enyl);
5β-(2'-bromo-3'-oxo-4'R-methyl-5'-cyclohexyl-pent-1'-trans-1'-enyl);

2β-hydroxy-cyclopentan-1β-acetic acid-γ-lactones:

5α-(2'-bromo-3'-oxo-4'R-methyl-non-1'-trans-1'-enyl);
5α-(2'-bromo-3'-oxo-oct-1'-trans-1'-enyl);
5α-(2'-bromo-3'-oxo-5'-oxa-non-1'-trans-1'-enyl);
5α-(2'-bromo-3'-oxo-4'S-methyl-oct-1'-trans-1'-enyl);
5α-(2'-bromo-3'-oxo-4'S-methyl-non-1'-trans-1'-enyl).

EXAMPLE 34

To a 0.02 M solution of zinc borohydride in ether (70 ml) is added a solution of 0.85 g of 2α-hydroxy-cyclopentan-1α-acetic acid-γ-lactone-5β-(2'-bromo-3'-oxo-4'S-methyl-oct-1'-trans-1'-enyl) in 25 ml of ethyl ether. This is stirred for 30 minutes, the excess reagent is destroyed by careful addition of 0.5 N sulfuric acid. The ether phase is separated off and washed to neutrality, dried and evaporated to dryness. The residue is chromatographed on silica gel, eluted with cyclohexane-methylene chloride, to give 0.62 g of 5β-(2'-bromo-3'S-hydroxy-4'S-methyl-oct-1'-trans-1'-enyl)-2α-hydroxy-cyclopentan-1α-acetic acid-γ-lactone and 0.22 g of the 3'R isomer.

EXAMPLE 35

At a temperature maintained between −7° and −5° C., a solution of 29 mg of NaBH$_4$ in 3 ml of methanol is added drop-wise into 0.43 g of 2β-hydroxy-cyclopentan-1β-acetic acid-γ-lactone-5α-(2'-bromo-3'-oxo-4'R-methyl-oct-1'-trans-1'-enyl) in 8 ml of methanol. This is stirred for 30 minutes and then 70 ml of saturated aqueous NaH$_2$PO$_4$ is added and the mixture extracted with ethyl acetate. From the organic phase, after evaporation of the solvent and chromatography on silica gel, eluted with cyclohexane-methylene chloride 2:8, one obtains 0.3 g of 2β-hydroxy-cyclopentan-1β-acetic acid-γ-lactone-5α-(2'-bromo-3'S-hydroxy-4'R-methyl-oct-1'-trans-1'-enyl) and 0.092 g of the R-isomer.

EXAMPLE 36

To 4.2 ml of a 0.25 M solution of lithium tri-sec.-butyl borohydride is added (at −30° C.) a solution of 357 mg of 5β-(2'-bromo-3'-oxo-4'S-methyl-non-1'-trans-1'-enyl)-2α-hydroxy-cyclopentan-1α-acetic acid-γ-lactone. After stirring for 45 minutes the excess reagent is destroyed by addition of 2 ml of acetone. This is neutralized with monosodium phosphate and evaporated under vacuum. The residue is taken up in methylene chloride and after evaporation of the solvent from the organic phase the residue is chromatographed on silica gel, eluted with methylene chloride, yielding 0.28 g of 5β-(2'-bromo-3'S-hydroxy-4'S-methyl-non-1'-trans-1'-enyl)-2α-hydroxy-cyclopentan-1α-acetic acid-γ-lactone.

EXAMPLE 37

Using one of the procedures described in examples 34 and 36 by reduction of the trans-enone prepared as described in examples 30 to 33, with the hydride either NaBH$_4$, Zn(BH$_4$)$_2$ of lithium tri-sec.-butyl-borohydride, the following allylic alcohols are obtained:

2α-hydroxy-cyclopentan-1α-acetic acid-γ-lactones:

5β-(2'-bromo-3'S-hydroxy-oct-1'-trans-1'-enyl);
5β-(2'-bromo-3'S-hydroxy-non-1'-trans-1'-enyl);
5β-(2'-bromo-3'S-hydroxy-dec-1'-trans-1'-enyl);
5β-(2'-bromo-3'S-hydroxy-4'R-methyl-oct-1'-trans-1'-enyl);
5β-(2'-bromo-3'S-hydroxy-4'R-methyl-non-1'-trans-1'-enyl);
5β-(2'-bromo-3'S-hydroxy-5'-oxa-oct-1'-trans-1'-enyl);
5β-(2'-bromo-3'S-hydroxy-5'-oxa-non-1'-trans-1'-enyl);
5β-(2'-bromo-3'S-hydroxy-4'R-methyl-5'-oxa-oct-1'-trans-1'-enyl);
5β-(2'-bromo-3'S-hydroxy-4'S-methyl-5'-oxa-oct-1'-trans-1'-enyl);
5β-(2'-bromo-3'S-hydroxy-5'-cyclopentyl-pent-1'-trans-1'-enyl);
5β-(2'-bromo-3'S-hydroxy-5'-cyclohexyl-pent-1'-trans-1'-enyl);
5β-(2'-bromo-3'S-hydroxy-5'-phenyl-pent-1'-trans-1'-enyl);
5β-(2'-bromo-3'S-hydroxy-5'-p-chlorophenyl-pent-1'-trans-1'-enyl);
5β-(2'-bromo-3'S-hydroxy-5'-cyclohexyloxy-pent-1'-trans-1'-enyl);
5β-(2'-bromo-3'S-hydroxy-5'-phenoxy-pent-1'-trans-1'-enyl);
5β-(2'-bromo-3'S-hydroxy-4'R-methyl-5'-cyclohexyl-pent-1'-trans-1'-enyl);

2β-hydroxy-cyclopentan-1β-acetic acid-γ-lactones:

5α-(2'-bromo-3'S-hydroxy-1'R-methyl-non-1'-trans-1'-enyl);
5α-(2'-bromo-3'S-hydroxy-oct-1'-trans-1'-enyl);
5α-(2'-bromo-3'S-hydroxy-5'-oxa-non-1'-trans-1'-enyl);
5α-(2'-bromo-3'S-hydroxy-non-1'-trans-1'-enyl);
5α-(2'-bromo-3'S-hydroxy-4'S-methyl-oct-1'-trans-1'enyl);
5α-(2'-bromo-3'S-hydroxy-4'S-methyl-non-1'-trans-1'-enyl); and their 3'R-hydroxy isomers.

EXAMPLE 38

A solution of 0.69 g of 2α-hydroxy-5β-(2'-bromo-3'S-hydroxy-4'R-methyl-oct-1'-trans-1'-enyl)-cyclopentan-1α-acetic acid-γ-lactone in anhydrous benzene is treated with 0.26 g of 4-methoxy-5,6-dihydro-2H-pyran and with a benzene solution containing 3.5 mg of p-toluene-sulfonic acid. This is left overnight at room temperature, then the organic phase is washed with 5% sodium bicarbonate and water until neutral and evaporated to dryness, to give 0.91 g of 2α-hydroxy-5β-(2'-bromo-3'S-hydroxy-4'R-methyl-oct-1'-trans-1'-enyl)-cyclopentan-1α-acetic acid-γ-lactone-3'-(4''-methoxy-4''-tetrahydropyranylether).

EXAMPLE 39

If, in the procedures outlined in examples 38 the vinylic ether is replaced with 1,4-dioxane, starting from 2β-hydroxy-cyclopentan-1β-acetic acid-γ-lactone-5α-(2'-bromo-3'S-hydroxy-4'R-methyl-non-1'-trans-1'-enyl) ($3.5 \cdot 10^{-3}$ moles) in benzene and reacting with $3.72 \cdot 10^{-3}$ moles of 1,4-dioxane in the presence of $3.5 \cdot 10^{-5}$ moles of p-toluene-sulfonic acid, one obtains $3.5 \cdot 10^{-3}$ moles of 2β-hydroxy-5α-(2'-bromo-3'S-hydroxy-4'R-methyl-non-1'-trans-1'-enyl)-cyclopentan-1β-acetic acid-γ-lactone-3'-DIOX-ether.

EXAMPLE 40

Proceeding as in examples 38 and 39 and starting with alcohols prepared as described in examples 34, 35, 36 and 37, reaction with one of the vinyl ethers (1-methoxy-5,6-dihydro-2H-pyran, 3-methoxy-5,6-dihydro-2H-pyran, 2,3-dihydro-pyran or 4,4-dioxane) one obtains the corresponding 3'-(4''-methoxy-4''-tetrahydropyranylethers, the 3'-(3''-methoxy-3''-tetrahydropyranylethers, the 3'-(2'-tetrahydropyranylethers) or the 3'-(2'-dioxanylethers).

EXAMPLE 41

A solution of 0.9 g of 2α-hydroxy-5β-(2'-bromo-3'S-hydroxy-4'R-methyl-oct-1'-trans-1'-enyl)-cyclopentan-1α-acetic acid-γ-lactone-3'-(4''-methoxy-4''-tetrahydropyranylether) in 40 ml of anhydrous toluene is cooled to −60° C. and, under an atmosphere of inert gas, 7.6 ml of a 0.5 M solution of diisobutylaluminium hydride in toluene is added. This is allowed to stand for 30 minutes at −60° C., then 7 ml of 2H isopropanol in toluene are added and the mixture allowed to return to room temperature. With constant stirring, add 0.8 ml of water, 2 g of anhydrous sodium sulfate and 2 g of filter earth. Filter and evaporate to dryness to obtain 0.9 g of pure 2α-hydroxy-5β-(2'-bromo-3'-S-hydroxy-4'R-methyl-oct-1'-trans-1'-enyl)-cyclopentan-1α-ethanal-γ-lactol-3'-(4''-methoxy-4''-tetrahydropyranylether).

EXAMPLE 42

Using the procedure of example 41 for reduction of the -γ-lactone-acetalic ethers, for example those of example 40, with DIBA, one obtains the acetalic ethers (2''-THP-ethers, 2''-DIOX-ethers, 4''-methoxy-4''-THP-ethers, 3''-methoxy-3''-THP-ethers) of the following γ-lactols:

2α-hydroxy-cyclopentan-1α-ethanal-γ-lactols:

5β-(2'-bromo-3'S-hydroxy-oct-1'-trans-1'-enyl);
5β-(2'-bromo-3'S-hydroxy-non-1'-trans-1'-enyl);
5β-(2'-bromo-3'S-hydroxy-dec-1'-trans-1'-enyl);
5β-(2'-bromo-3'S-hydroxy-4'R-methyl-oct-1'-trans-1'-enyl);
5β-(2'-bromo-3'S-hydroxy-4'R-methyl-non-1'-trans-1'-enyl;
5β-(2'-bromo-3'S-hydroxy-5'-oxa-oct-1'-trans-1'-enyl);
5β-(2'-bromo-3'S-hydroxy-5'-oxa-non-1'-trans-1'-enyl);
5β-(2'-bromo-3'S-hydroxy-4'R-methyl-5'-oxa-oct-1'-trans-1'-enyl);
5β-(2'-bromo-3'S-hydroxy-4'S-methyl-5'-oxa-oct-1'-trans-1'-enyl);
5β-(2'-bromo-3'S-hydroxy-5'-cyclopentyl-pent-1'-trans-1'-enyl);

5β-(2′-bromo-3′S-hydroxy-5′-cyclohexyl-pent-1′-trans-1′-enyl);

5β-(2′-bromo-3′S-hydroxy-5′-phenyl-pent-1′-trans-1′-enyl);

5β-(2′-bromo-3′S-hydroxy-5′-p-chlorophenyl-pent-1′-trans-1′-enyl);

5β-(2′-bromo-3′S-hydroxy-5′-cyclohexyloxy-pent-1′-trans-1′-enyl);

5β-(2′-bromo-3′S-hydroxy-5′-phenoxy-pent-1′-trans-1′-enyl);

5β-(2′-bromo-3′S-hydroxy-4′R-methyl-5′-cyclohexyl-pent-1′-trans-1′-enyl);

2β-hydroxy-cyclopentan-1β-ethanal-β-lactols:

5α-(2′-bromo-3′S-hydroxy-4′R-methyl-non-1′-trans-1′-enyl);

5α-(2′-bromo-3′S-hydroxy-oct-1′-trans-1′-enyl);

5α-(2′-bromo-3′S-hydroxy-5′-oxa-non-1′-trans-1′-enyl);

5α(2′-bromo-3′S-hydroxy-non-1′-trans-1′-enyl);

5α-(2′-bromo-3′S-hydroxy-4′S-methyl-oct-1′-trans-1′-enyl);

5α-(2′-bromo-3′S-hydroxy-4′S-methyl-non-1′-trans-1′-enyl); and their 3′R-isomers.

EXAMPLE 43

Saturate by bubbling a stream of nitrogen gas through a solution of 0.32 g of 5c-9-oxo-15S-hydroxy-16S-methyl-prost-5-en-13-ynoic acid in anhydrous ethyl ether. The ammonium salt precipitate is filtered out and dried under vacuum at 4° C., then stored at −10° C.

EXAMPLE 44

A solution of 3.1 g of 2β,4β-dihydroxy-3α-iodo-5α-methoxy-methylether-cyclopentan-1β-acetic acid-γ-lactone, 5.24 g of triphenylphosphine and 1.21 g of acetic acid in 30 ml of THF is combined with a solution of 3.48 g of ethyl azobisphoxylate. This is stirred for 2 hours then evaporated to dryness. The residue is chromatographed on silica gel with cyclohexane-ethyl ether, yielding 0.49 g of 2β-hydroxy-cyclopent-3-en-1β-acetic acid-γ-lactone-5α-methoxy-methylether, m.p. 47°–48° C., $[\alpha]_D = -256°$.

By the same method, if one starts with the corresponding 5α-benzyloxy-methyl and the 2α,4α-dihydroxy-3β-iodo-5β-methoxymethyl ether- (or with the 5β-benzyloxy-methylether)-cyclopentan-1α-acetic acid-γ-lactone, the following compounds are prepared:

2β-hydroxy-cyclopent-3-en-1β-acetic acid-γ-lactone-5α-hydroxy-methyl-benzyl ether;

2α-hydroxy-cyclopent-3-en-1α-acetic acid-γ-lactone-5β-hydroxy-methyl-benzyl ether;

2α-hydroxy-cyclopent-3-en-1α-acetic acid-γ-lactone-5β-hydroxy-methyl-methyl ether.

EXAMPLE 45

Stir a suspension of 0.31 g of sodium hydride (80% dispersion in mineral oil) in 35 ml of dimethoxyethane and add drop by drop a solution of 2.5 g of (2-oxo-3S-methyl-heptyl)-dimethoxy-phosphonate in 15 ml of dimethoxyethane. When hydrogen evolution no longer occurs, add 1.9 g of N-bromo-succinimide and continue to stir for 30 minutes, thus forming the sodium derivative of (1-bromo-2-oxo-3S-methyl-heptyl)-dimethoxy-phosphonate. Next add a solution of 1 g of dl-5β-formyl-cyclopentan-2α-hydroxy-1α-acetic acid-γ-lactone in 10 ml of dimethoxyethane. Stir for 1 hour then dilute with 6 volumes of benzene, wash with aqueous 5% sodium chloride solution until neutral. Dry over Na₂SO₄ and evaporate to dryness. The residue is chromatographed on silica gel, eluted with methylene chloride-ethyl ether (97:3), to give 1.85 g of dl-5β-(2′-bromo-3′-oxo-4′S-methyl-oct-1′-trans-1′-enyl)-2α-hydroxy-cyclopentan-1α-acetic acid-γ-lactone, λmax 250 mμ (E=9,800). A solution of 2.5 g of this product in anhydrous ethyl ether is added drop by drop to a 0.10 M solution of zinc borohydride in 100 ml of ethyl ether. After stirring for 30 minutes, the excess reagent is decomposed with 4 N H₂SO₄. The mixture is washed with water until neutral and evaporated to dryness, giving a mixture of 1-epimeric alcohols that can be separated by column chromatography. When this residue is chromatographed on a 350 silica gel column, eluted with methylene chloride, the following are obtained:

nat-5β-(2′-bromo-3′S-hydroxy-4′S-methyl-oct-1′-trans-1′-enyl)-cyclopentan-2α-hydroxy-1α-acetic acid-γ-lactone, $[\alpha]_D = -13°$; $[\alpha]_{365°} = -41°$ (chloroform), 0.9 g;

ent-5β-(2′-bromo-3′S-hydroxy-4′S-methyl-oct-1′-trans-1′-enyl)-cyclopentan-2α-hydroxy-1α-acetic acid-γ-lactone (also called 5α-(2′-bromo-3′R-hydroxy-1′S-methyl-oct-1′-trans-1′enyl)-cyclopentan-2β-hydroxy-1β-acetic acid-γ-lactone); $[\alpha]_D = +2.6°$; $[\alpha]_{365°} = +12°$; (chloroform), 0.34 g;

ent-5β-(2′-bromo-3′R-hydroxy-4′S-methyl-oct-1′-trans-1′-enyl)-cyclopentan-2α-hydroxy-1α-acetic acid-γ-lactone (also called 5α-(2′-bromo-3′S-hydroxy-4′S-methyl-oct-1′-trans-1′-enyl)-cyclopentan-2β-hydroxy-1β-acetic acid-γ-lactone); $[\alpha]_D = +19.6°$; $[\alpha]_{365°} = +80°$ (chloroform); 0.62 g;

and finally, nat-5β-(2′-bromo-3′R-hydroxy-4′S-methyl-oct-1′-trans-1′-enyl)-cyclopentan-2α-hydroxy-1α-acetic acid-γ-lactone, $[\alpha]_D = -28°$, $[\alpha]_{365°} = -105°$; 0.38 g.

To a solution of 0.89 g of the first alcohol 5β-(2′-bromo-3′S-hydroxy-4′S-methyl-oct-1′-trans-1′-enyl)-cyclopentan-2α-hydroxy-1α-acetic acid-γ-lactone in 10 ml of methylene chloride, add 0.26 g of 2,3-dihydropyran and 6 mg of p-toluene-sulfonic acid. Let stand for two hours at room temperature, add 0.2 ml of pyridine and evaporate to dryness, to give 1.01 g of 5β-(2′-bromo-3′S-hydroxy-4′S-methyl-oct-1′-trans-1′-enyl)-cyclopentan-2α-hydroxy-3′-tetrahydropyranylether-1α-acetic acid-γ-lactone, $[\alpha]_D = -19.8°$, $[\alpha]_{365°} = -58°$ (CHCl₃).

This compound is dried with benzene, dissolved in anhydrous toluene and cooled to −60°. Over a 15 minutes period, 10.4 ml of a 0.5 M solution of diisobutylaluminium hydride in toluene is added. After stirring for 40 minutes at −60° C., decompose the excess reagent by adding dropwise a 2 M solution of isopropanol, maintaining the reaction at −60° C. Then warm to room temperature and add 0.9 ml of water, 1.2 g of filter earth and 3 g of sodium sulfate. Filter and evaporate to dryness. Under nitrogen, add to a solution of 1.01 g of the lactol obtained above in 1.1 ml of dimethylsulfoxide a solution of the ylide prepared by adding under nitrogen 1.14 g of potassium tert-butylate to a solution of 2.21 g of triphenyl-(4-carboxybutyl)-phosphonium bromide in 8 ml of dimethylsulfoxide. Stir for 3 hours, then dilute with 3 ml of 1 N KOH and 10 ml of water. Extract with ethyl ether to remove the triphenylphosphoxide. The ether extracts are re-extracted with 3×5 ml of 0.5 N KOH and then discarded. The combined alkaline phases are acidified to pH 4.8 and extracted with ethyl ether-pentene 50:50. The organic extracts are washed twice with 5 ml of saturated ammonium sulfate solution, dried and evaporated to dryness, yielding 1.1 g of 5c-16S-methyl-9α,15S-dihydroxy-prost-5-en-13-ynoic acid-15-tetrahydropyranylether, m/e (M+434) (M+—H₂O 412), (M+—84 350. This compound is dissolved in 30 ml of acetone and cooled to −15° to −20° C., then 1 ml of Jones reagent is added, and the reaction mixture let stand at the low temperature for 2 hours. It is then diluted with 80 ml of benzene, the organic phase is washed with saturated ammonium sulfate solution and evaporated to dryness, to give 1.06 g of 5c-16S-methyl-9-oxo-15S-hydroxy-prost-5-en-13-ynoic acid-15-tetrahydropyranylether. This is dissolved in 60 ml of acetone and warmed to 36° C. after addition of 50 ml of 0.1 N aqueous oxalic acid. After 8 hours at 36° C., the acetone is removed under vacuum. The aqueous phase is extracted with ethyl acetate. The organic phase is washed until neutral with saturated ammonium sulfate solution and evaporated to dryness.

The residue is chromatographed on silica gel, eluted with methylene chloride-cyclohexane 80:20 and 90:10 and finally with methylene chloride alone, giving 0.68 g of 5cis-16S-methyl-g-oxo-15S-hydroxy-prost-5-en-12-ynoic acid, an oil, $[\alpha]_D = +4.2°, [\alpha]_{365°} = -38°$(EtOH) (also called 11-deoxy-16S-methyl-13-dehydro-PGE₂).

Proceeding as described above and starting with the other alcohols, the following compounds are obtained:
5cis-16S-methyl-9-oxo-15R-hydroxy-3,12-diiso-prost-5-en-13-ynoic acid, $[\alpha]_D = -5.1°$, $[\alpha]_{365°} = +57°$(EtOH) (also called ent-11-deoxy-16S-methyl-13-dehydro-PGE₂);
5c-16S-methyl-9-oxo-15S-hydroxy-8,12-diiso-prost-5-en-13-ynoic acid (also called ent-11-deoxy-16S-methyl-15-epi-PGE₂) $[\alpha]_D = -10°, [\alpha]_{365°} = +63°$ (EtOH);
5c-16S-methyl-9-oxo-15R-hydroxy-prost-5-en-13-ynoic acid (also called 11-deoxy-16S-methyl-13-dehydro-15-epi-PGE₂), $[\alpha]_D = +9.3°$, $[\alpha]_{365°} 32 - 54°$ (EtOH).

EXAMPLE 46

Over a 30 minutes period add dropwise to a suspension of 676 mg of 30% sodium hydride in 90 ml of dimethoxyethane a solution of (2-oxo-3R-methyl-heptyl)-dimethoxyphosphonate in 10 ml of dimethoxyethane. Stir for 30 minutes longer and then add 4.15 g of N-bromo-succinimide and stir for another 30 minutes. Add 2.5 g of 5α-formyl-2α-hydroxy-cyclopentan-1β-acetic acid-γ-lactone, $[\alpha]_D = +25.3°$ (CHCl₃), in 10 ml of benzene and stir for one hour. Add 30 ml of saturated monobasic sodium phosphate and 90 ml of benzene. Separate the organic phase, dry it over Na₂SO₄ and evaporate to dryness. The residue is chromatographed on silica gel, eluted with dichloromethane-cyclohexane 70:30, to give 2.98 g of 5α-(2'-bromo-3'-oxo-4'R-methyl-oct-1'-trans-1'-enyl)-cyclopentan-2β-hydroxy-1β-acetic acid-γ-lactone, χmax 252 mμ, E=8,900.

This compound is dissolved in 100 ml of anhydrous ethyl ether and added dropwise to 180 ml of a 0.07 N solution of zinc borohydride in ethyl ether. After 30 minutes this is treated with 4N sulfuric acid and 25 ml of saturated sodium chloride solution. The organic phase is washed to neutral, evaporated to dryness and chromatographed on 150 g of silica gel, eluted with cyclohexane-methylene chloride (30:70, 20:80 and finally 10:90), yielding 1.86 g of 5α(2'-bromo-3'R-hydroxy-4'R-methyl-oct-1'-trans-1'-enyl)-cyclopentan-2β-hydroxy-1α-acetic acid-γ-lactone, $[\alpha]_D = +17°$, $[\alpha]_{365} = +49.5°$, and 0.33 g of 5α-(2'-bromo-3'S-hydroxy-4'R-methyl-oct-1'-trans-1'-enyl)2β-hydroxy-cyclopentan-1α-acetic acid-γ-lactone, $[\alpha]_D = +34°$, $[\alpha]_{365°} = +129°$. Reaction of the first of these two pimeric alcohols with 2,3-dihydropyran (0.8 ml) in 15 ml of dichloromethane, in the presence of p-toluene-sulfonic acid, gives the corresponding 3'R-tetrahydropyranylether, wich is then reacted at −60° C. with 2 molar equivalents of diisobutylaluminium hydride to give the corresponding lactol 5α-(2'-bromo-3'R-hydroxy-4'R-methyl-oct-1'-trans-1'-enyl)-cyclopentan-2β-hydroxy-1α-ethanal-γ-lactol-3'-THP-ether, $[\alpha]_D = +12°$ (chloroform). To a solution of 1.65 g of this compound in 5 ml of dimethyl-sulfoxide, add the ylide prepared from 16.6 g of triphenyl-(1-carboxy-butyl)-phosphonium bromide and 1.4 g of sodium hydride in 45 ml of dimethylsulfoxide. Let stand for 30 minutes at 20° C., then dilute with 20 ml of 1 N NaOH and 20 ml of water, and remove the triphenylphosphoxide by extraction with ethyl ether. Acidify the alkaline phase to pH 4.8 and extract with ethyl ether:pentane 1:1. After evaporation of the solvent, one obtains 1.2 g of 5c-9β,15R-dihydroxy-16R-methyl-8,12-diiso-prost-5-en-13-ynoic acid -15-tetrahydropyranylether, which is dissolved in 40 ml of acetone, cooled to −10° to −12° C. and oxidized by addition of 3 ml of Jones reagent. After 40 minutes at −10° C., dilute with saturated ammonium sulfate solution, dry over sodium sulfate and evaporate to dryness. The residue (1.08 g) is dissolved in 100 ml of acetone and combined with 110 ml of 0.1N oxalic acid and warmed for 60 hours at 40° C.

The acetone is evaporated off under vacuum, the residue is extracted with ethyl acetate and organic phase evaporated to dryness. The residue is chromatographed on silica gel, eluted with methylene chloride, to give 0.6 g of 5c-9-oxo-15R-hydroxy-16R-methyl-8,12-diiso-prost-5-en-13-ynoic acid or ent-16R-methyl-11-deoxy-13-dehydro-PGE₂, an oil, $[\alpha]_D = -2.3°$, $[\alpha]_{365°} = +131°$ (EtOH).

In the same way, beginning with the other epimeric alcohol, one prepares the 5c-9-oxo-15S-hydroxy-16R-methyl-8,12-diiso-prost-5-en-13ynoic acid, $[\alpha]_D = -11°, [\alpha]_{365} = +159°$ (EtOH).

EXAMPLE 47

A solution of 8.64 g of (2-oxo-3S-methyl-3R-fluoro-heptyl)-dimethoxy-phosphonate is added, dropwise, to a stirred suspension of sodium hydride (80% dispersion in mineral oil, 1.02 g). When no more hydrogen evolves, the mixture is treated with N-bromo-succinimide (6.14 g) and stirred for 30 minutes so obtaining the sodium salt of (1-bromo-2-oxo-3S-methyl-3-fluoro-heptyl)-dimethoxy-phosphonate. Then a solution of 5α-formyl-cyclopentane-2α-hydroxy-1α-acetic acid-γ-lactone (4.6 g) in benzene (30 ml) is added to the bromo phosphonate solution. The reaction mixture is stirred for one hour at room temperature, washed with aqueous 10% NaH₂PO₄ solution, dried over Na₂SO₄ and evaporated to dryness. The residue is chromatographed on silica gel (250 g) and eluted with benzene-methylene chloride (60:40), to give 8.21 g of 5β-(2'-bromo-3'-oxo-4'S-methyl-4'R-fluoro-oct-1'-trans-1'-enyl)-2α-hydroxy-cyclopentane-1α-acetic acid-γ-lactone (χ_{max}=251 mμ; E=9,250). By reduction of this compound with sodium borohydride (1.1 g) in methylene chloride:ethanol (1:1) (120 ml) at −10°, and usual work up, a mixture of the epimeric alcohols is obtained (8.1 g) which is chromatographed on 0.9 kg of silica gel to afford 3.6 g of 5β-(2'-bromo-3'S-hydroxy-4'S-methyl-4'R-fluoro-oct-1'-trans-1'-enyl)-2α-hydroxy-cyclopentane-1α-acetic acid-γ-lactone, and 2.9 g of the epimeric 3'R-hydroxy derivative.

A solution of the 3'S-alcohol in methylene chloride is treated at room temperature with 2,3-dihydropyran (1.68 g) and p-toluenesulfonic acid (25 mg) and then after three hours with pyridine (0.12 ml). After removal of the solvents in vacuo, the crude residue 5β-(2'-bromo-3'S-hydroxy-4'S-methyl-4'R-fluoro-oct-1'-trans-1'-enyl)-2α-hydroxy-cyclopentane-1α-acetic acid-γ-lactone-3'-THP-ether is dissolved in dry toluene. Under a nitrogen atmosphere this stirred solution, cooled at −60°, is treated over 20 minutes with a 0.5M diisobutyl aluminium hydride solution (40 ml). The mixture is stirred for 30 minutes at −60° C. and then treated with 20 ml of a 2M isopropanol solution in toluene. The mixture is heated to room temperature, treated with water, sodium sulfate and celite, filtered. The filtrate is evaporated to dryness in vacuum to afford 4.3 g of crude 5β-(2'-bromo-3'S-hydroxy-4'S-methyl-4'R-fluoro-oct-1'-trans-1'-enyl)-2α-hydroxy-cyclopentane-1α-ethanal-γ-lactol-3'-THP-ether, which is reacted with the ylide prepared from 16.6 g of triphenyl-(4-carboxy-butyl)-phosphonium bromide and 1.44 g of sodium hydride in 45 ml of dimethylsulphoxide. Let stand for one hour at 20° C. and then after dilution with 1N NaOH (20 ml) and water (20 ml) remove the triphenylphosphoxide by extraction with ethylether. Acidification of aqueous alkaline phases to pH 4.5, extract on with pentane:ethyl ether (1:1), evaporation of the solvents in vacuo afforded 3.48 g of 5c-9α,15S-dihydroxy-16S-methyl-16R-fluoro-prost-5-en-13-ynoic acid-15-THP-ether. A solution of 1.2 g of this compound in acetone (40 ml) is treated with 25 ml of 0.2N aqueous oxalic acid for 2 hours at reflux temperature. After removal of the acetone in vacuo the aqueous phase is extracted repeatedly with ether, the combined organic layers are washed with saturated ammonium sulfate solution, dried and evaporated in vacuo to dryness. The crude product is adsorbed on acid-washed silica gel (20 g/g) and subsequent elution with cyclohexane-methylene chloride allows to obtain 0.68 g of pure 5c-9α,15S-dihydroxy-16S-methyl-16R-fluoro-prost-5-en-13-ynoic acid.

Using a similar procedure and starting from the epimeric 3'R-hydroxyderivative, 5c-9α,15R-dihydroxy-16S-methyl-16R-fluoro-prost-5-en-13-ynoic acid and its 15-THP-ether derivative are obtained.

EXAMPLE 48

A stirred solution of 5c-9α,15S-dihydroxy-16S-methyl-16R-fluoro-prost-5-en-13-ynoic acid-15-THP-ether (1.4 g) in acetone (28 ml), cooled at −18°, is treated with Jones reagent [2.8 ml, prepared by adding concentrated sulphuric acid (61 ml) to chromic anhydride (70 g) in water (500 ml)]. The mixture is stirred at −10° to −12° C. for 20 minutes, diluted with benzene (80 ml), washed with saturated ammonium sulphate solution until neutral, dried (Na₂SO₄) and then evaporated to dryness in vacuo to yield, as an oil, 5c-9-oxo-15S-hydroxy-16S-methyl-16R-fluoro-prost-5-en-13-ynoic acid-15-THP-ether, which is dissolved in acetone (80 ml). This solution is treated for 4 hours with 0.2N aqueous oxalic acid (50 ml) at 45° C.; then, after removal of acetone in vacuo, the aqueous phase is repeatedly extracted with ether. The combined extracts are washed with saturated ammonium sulphate solution, dried on Na₂SO₄ and evaporated to dryness in vacuum. The residue (1.1 g) is adsorbed on an acid washed silica gel and then by elution with cyclohexane-methylene chloride (70:30) the 5c-9-oxo-15S-hydroxy-16S-methyl-16R-fluoro-prost-5-en-13-ynoic acid (0.72 g) is obtained.

Using the 15R-epimer in this procedure, the 5c-9-oxo-15R-hydroxy-16S-methyl-16R-fluoro-prost-5-en-13-ynoic acid is obtained.

EXAMPLE 49

Using the (2-oxo-3R-methyl-3S-fluoro-heptyl)-dimethoxy-phosphonat in the procedure of the examples 47 and 48, the following compound are obtained:

5c-9α,15S-dihydroxy-16R-methyl-16S-fluoro-prost-5-en-13-ynoic acid-15-THP-ether;

5c-9-oxo-15S-hydroxy-16R-methyl-16S-fluoro-prost-5-en-13-ynoic acid-15-THP-ether and their 15R-epimers which are deacetalized with acetone-0.2N aqueous oxalic acid to afford after chromatographic purification the following:

5c-9α,15S-dihydroxy-16R-methyl-16S-fluoro-prost-5-en-13-ynoic acid;

5c-9-oxo-15S-hydroxy-16R-methyl-16S-fluoro-prost-5-en-13-ynoic acid and their 15R-epimers.

We claim:

1. A compound of the formula

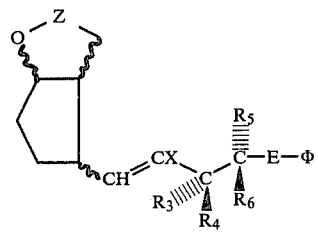

wherein:

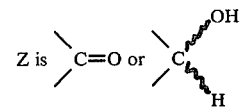

one of $R_3$ and $R_4$ is hydrogen and the other is a hydroxy group or a protecting group selected from

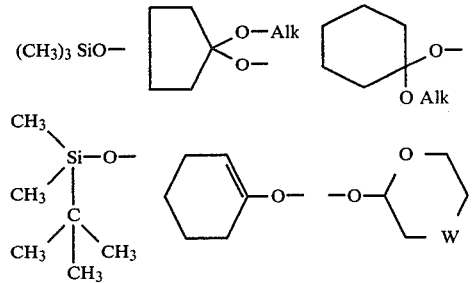

wherein

W is —O— or —CH₂— and Alk is a lower alkyl group, or when Z is C=O, $R_3$ and $R_4$, taken together, may also be a oxo group, X is chlorine, bromine or iodine;

$R_5$ and $R_6$ are independently hydrogen, fluorine or $C_1$–$C_4$ alkyl, provided that when either $R_5$ or $R_6$ is alkyl the other is hydrogen or fluorine and when one of them is fluorine the other is $C_1$–$C_4$ alkyl;

E is ─(CH₂)ₙ─ where n is an integer of 1 to 6 or ─(CH₂)ₙ₁─ O─(CH₂)ₙ₂─ where $n_1$, and $n_2$ are independently zero, 1, 2 or 3, Φ is methyl, cycloalkyl containing 3 to 7 ring carbon atoms optionally containing at least one ring oxygen or sulfur atom, phenyl, phenyl substituted by at least one of halogen, $C_1$–$C_4$ alkoxy, phenyl or trihalomethyl, provided that the chains bound to the C-8 and C-12 carbon atoms are in the trans configuration.

* * * * *